(12) United States Patent
Ure et al.

(10) Patent No.: US 11,241,551 B2
(45) Date of Patent: Feb. 8, 2022

(54) ENDOBRONCHIAL SUCTIONING DEVICE AND MEDICAL SUCTIONING SYSTEM FOR INTUBATED PATIENTS

(71) Applicants: John P. Ure, New Providence, NJ (US); Richard S. Teames, Pearland, TX (US)

(72) Inventors: John P. Ure, New Providence, NJ (US); Richard S. Teames, Pearland, TX (US)

( * ) Notice: Subject to any disclaimer, the term of this patent is extended or adjusted under 35 U.S.C. 154(b) by 454 days.

(21) Appl. No.: 16/211,544

(22) Filed: Dec. 6, 2018

(65) Prior Publication Data

US 2019/0105453 A1    Apr. 11, 2019

Related U.S. Application Data

(63) Continuation of application No. 14/634,803, filed on Feb. 28, 2015, now Pat. No. 10,149,956.

(51) Int. Cl.
| | | |
|---|---|---|
| *A61M 16/04* | (2006.01) | |
| *A61B 1/267* | (2006.01) | |
| *A61B 1/005* | (2006.01) | |

(52) U.S. Cl.
CPC ....... *A61M 16/0463* (2013.01); *A61B 1/0051* (2013.01); *A61B 1/0057* (2013.01); *A61B 1/2676* (2013.01); *A61M 16/0427* (2014.02); *A61M 16/0486* (2014.02); *A61M 16/0488* (2013.01); *A61M 2205/3375* (2013.01)

(58) Field of Classification Search
CPC .......... A61M 16/0463; A61M 16/0427; A61M 16/0488; A61M 16/0486; A61M 2205/3375; A61B 1/0051; A61B 1/0057; A61B 1/2676; A61B 34/71; A61B 2034/715

See application file for complete search history.

(56) References Cited

U.S. PATENT DOCUMENTS

| | | | | |
|---|---|---|---|---|
| 3,913,568 | A * | 10/1975 | Carpenter | A61B 1/0055 600/142 |
| 5,846,183 | A * | 12/1998 | Chilcoat | A61B 1/012 600/136 |
| 7,410,483 | B2 * | 8/2008 | Danitz | A61B 1/0053 606/1 |
| 2013/0137928 | A1 * | 5/2013 | Karasawa | A61B 1/0057 600/149 |
| 2013/0281925 | A1 * | 10/2013 | Benscoter | A61M 25/0147 604/95.04 |

* cited by examiner

*Primary Examiner* — Ariana Zimbouski
(74) *Attorney, Agent, or Firm* — Leavitt Eldredge Law Firm

(57) ABSTRACT

A medical suctioning system includes a device for insertion into an intubated patient's bronchi, the device including a controller end having actuating components that include a control mechanism coupled to a plurality of cables at the controller end, the controller end having a suction control button engaged with a plunger to allow for activation and deactivation of suction through the controller end; a control lever in communication with an articulating lever housed within the controller end, the articulating lever to engage with one or more cables disposed through the controller end and to engage with an articulating tip portion at a distal end opposite the controller end; and a catheter extending away from the controller end to the distal end.

10 Claims, 22 Drawing Sheets

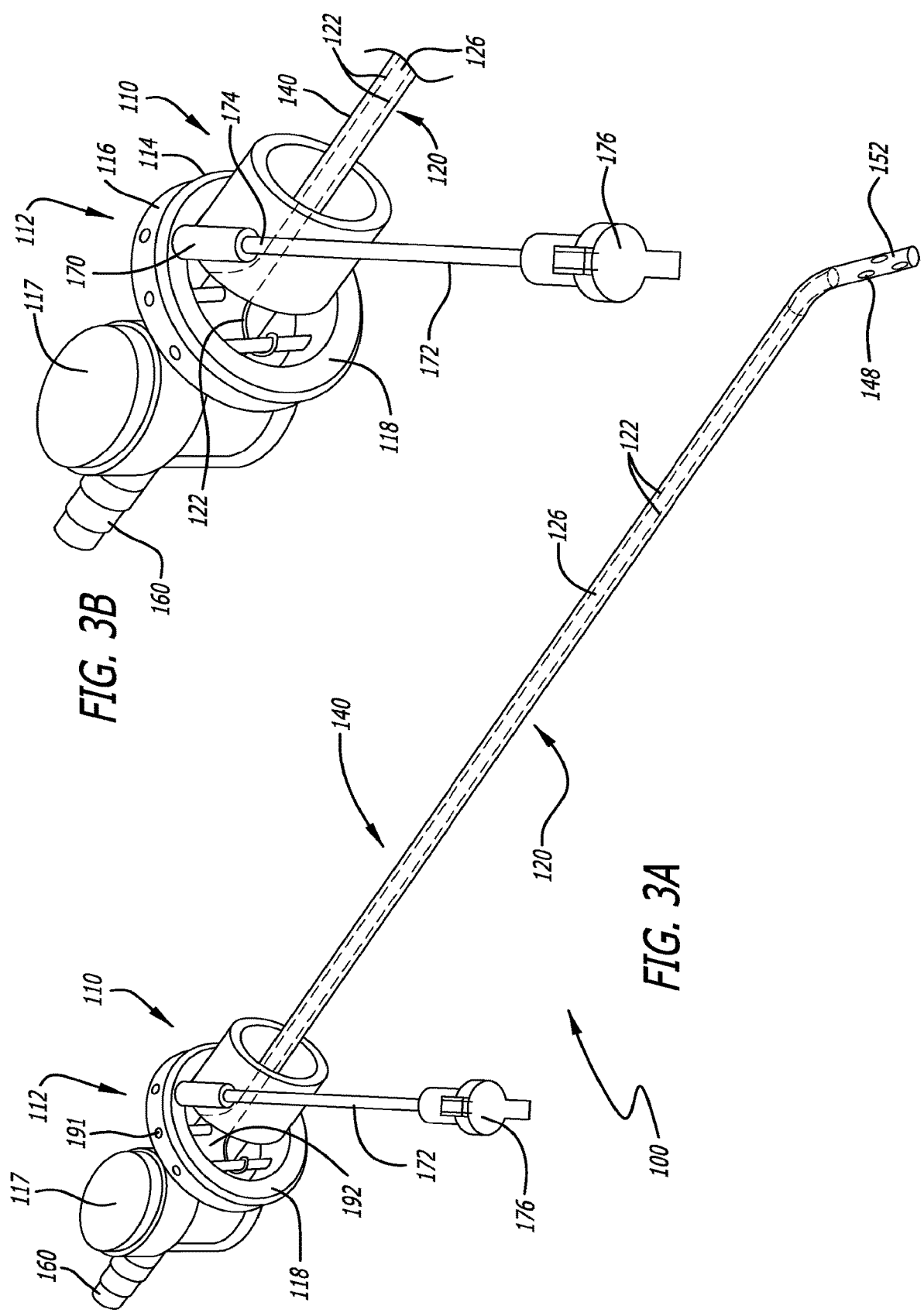

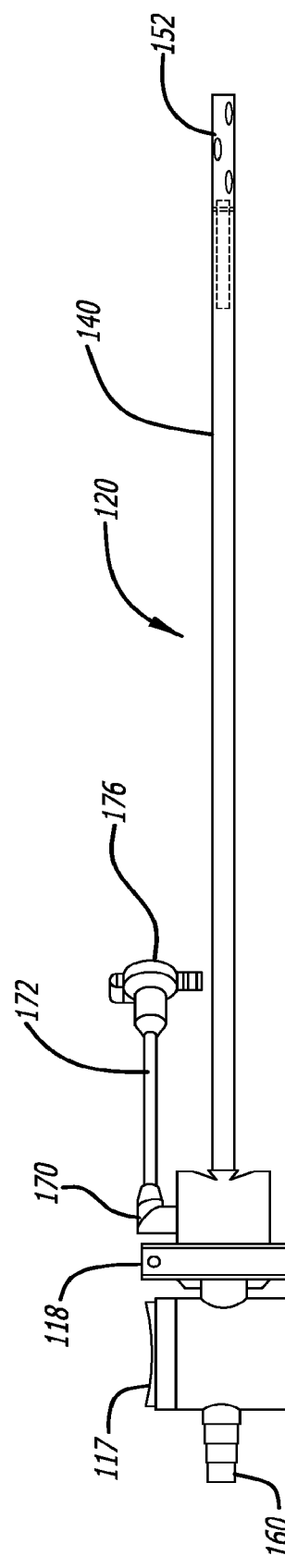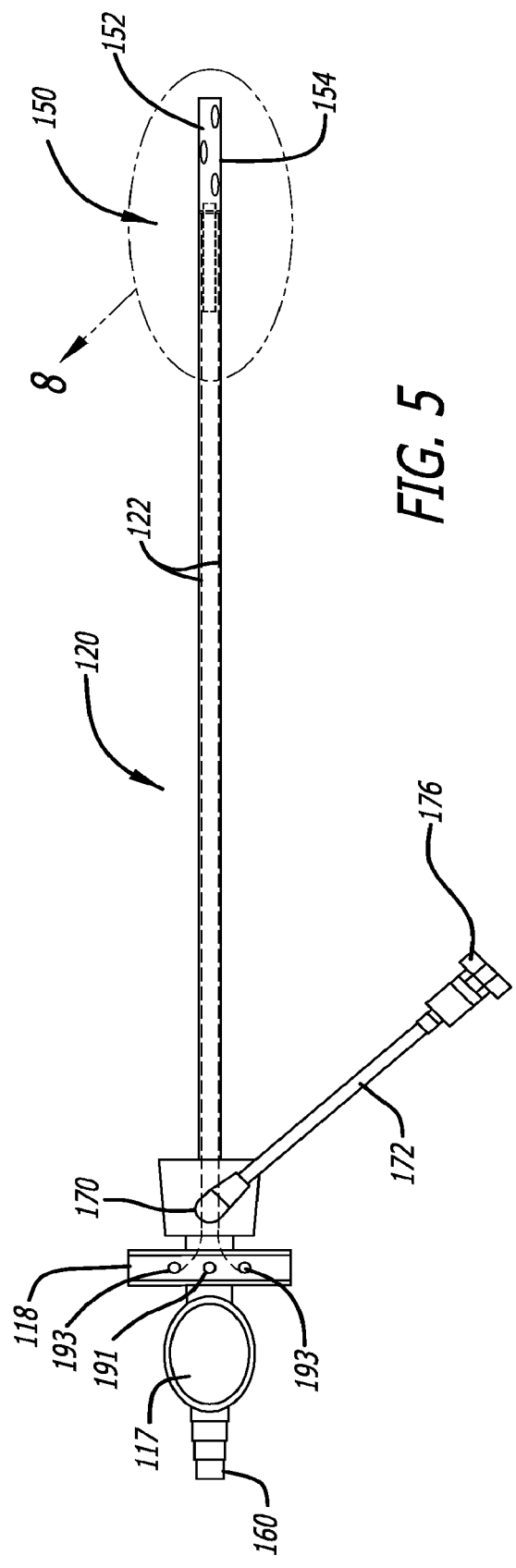

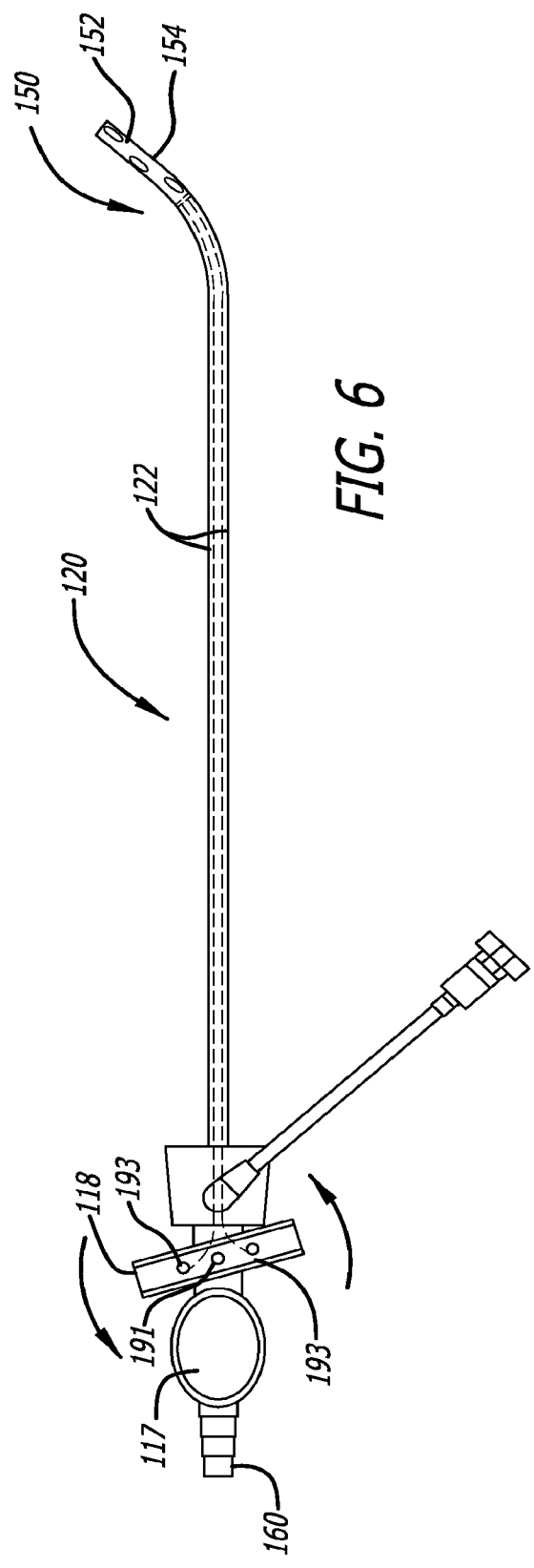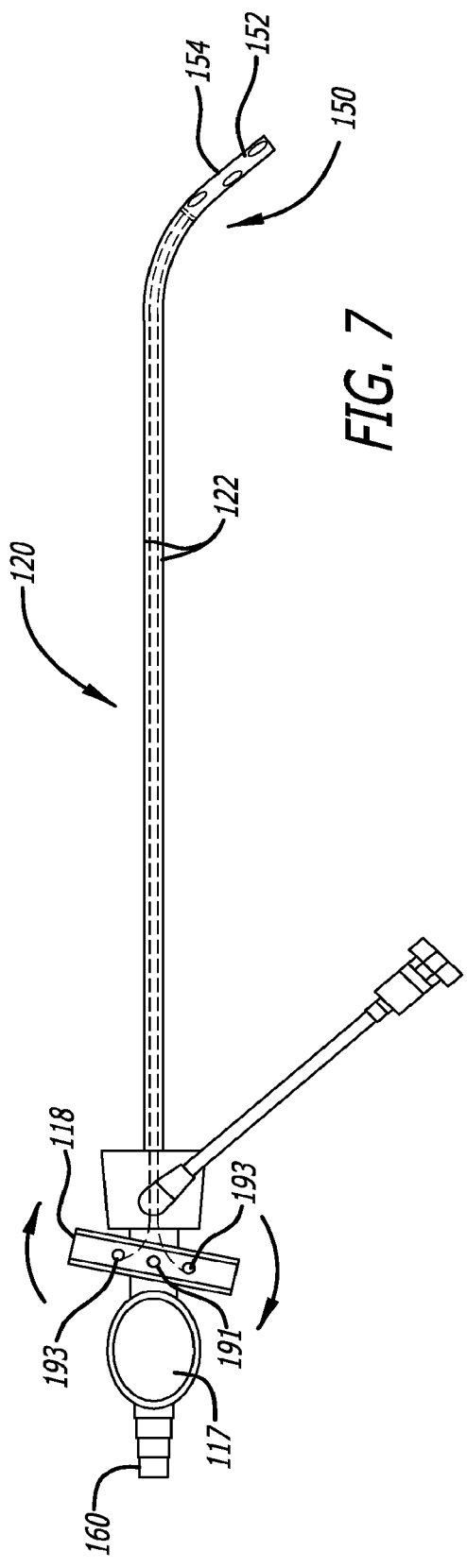

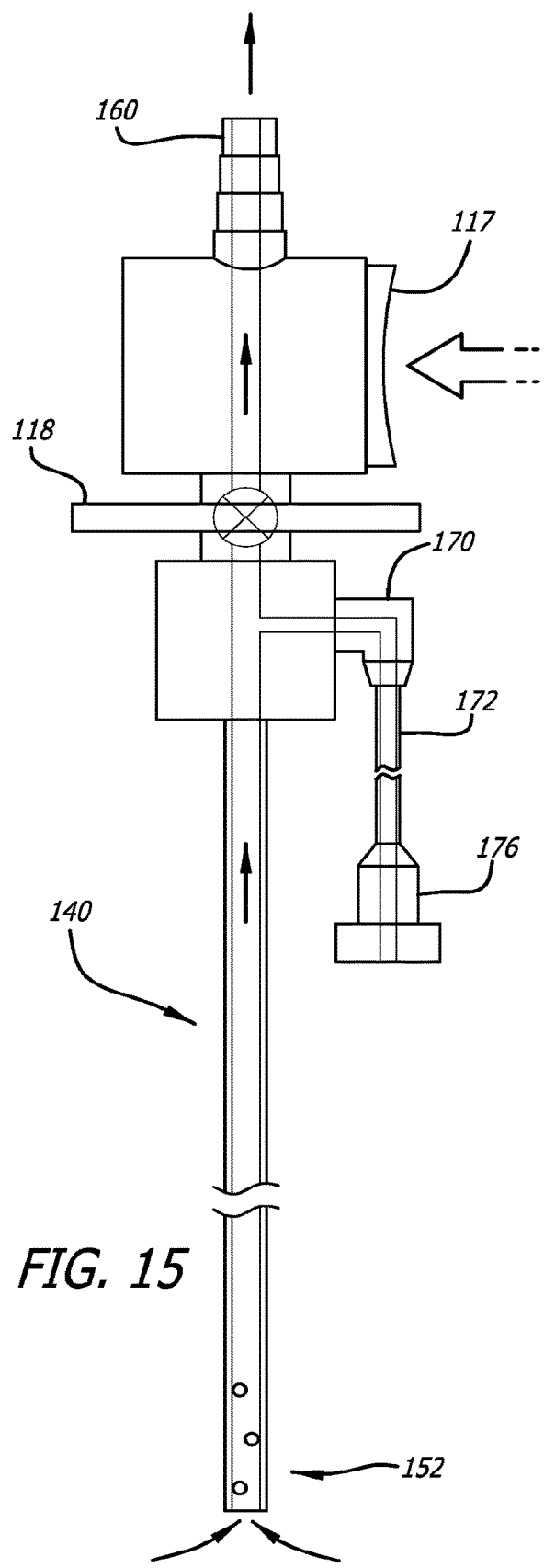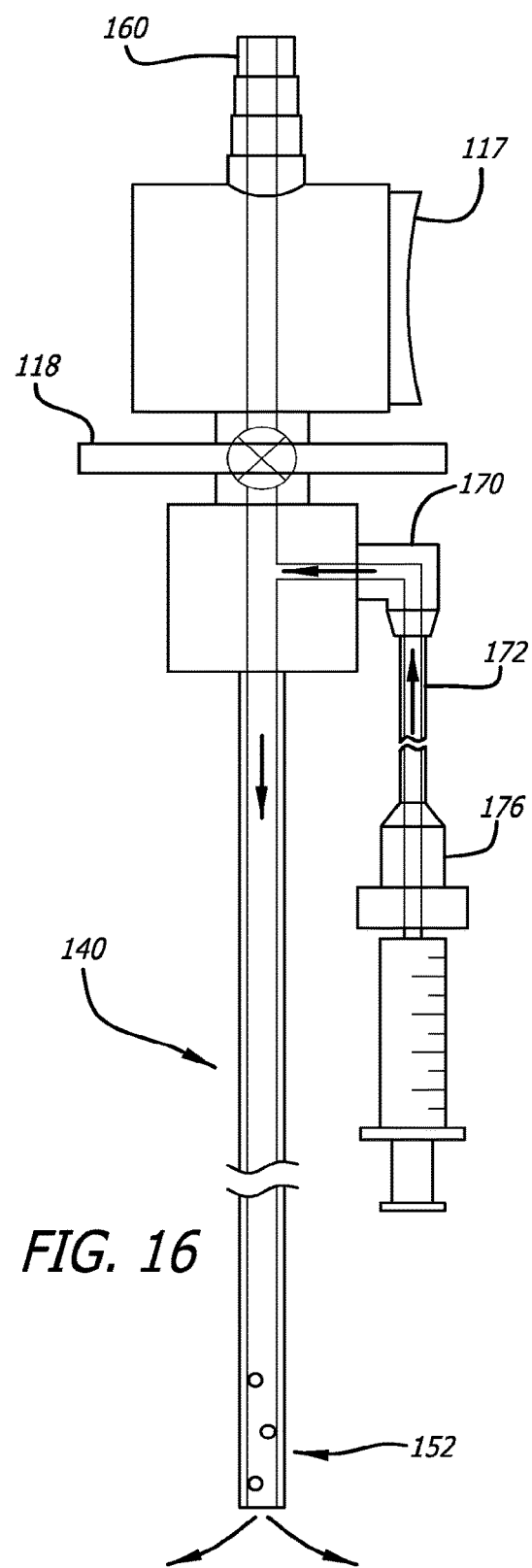

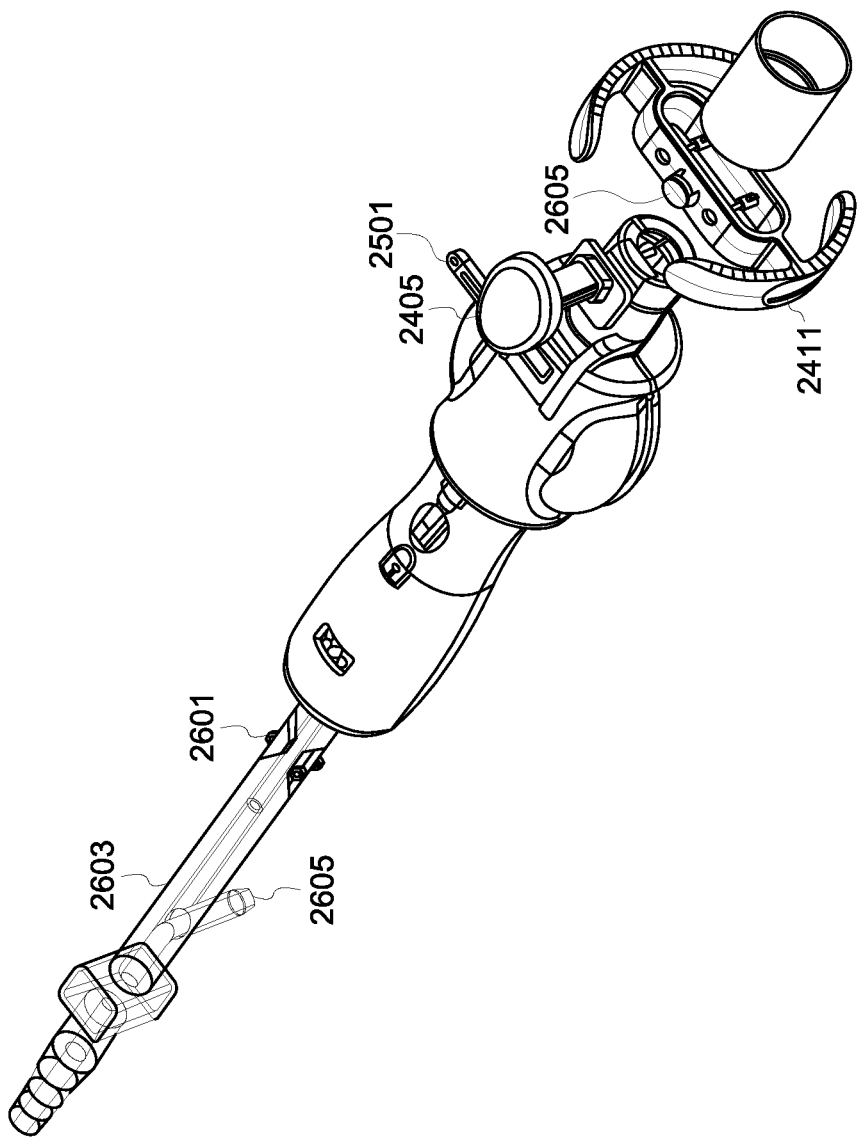
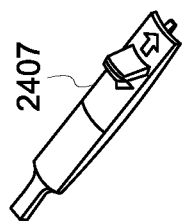
FIG. 26

ENDOBRONCHIAL SUCTIONING DEVICE AND MEDICAL SUCTIONING SYSTEM FOR INTUBATED PATIENTS

BACKGROUND

1. Field of the Invention

The present invention relates to devices for suctioning devices for use in the field of medicine. Specifically, the present invention relates to a catheter for use with an endobronchial tube or the like that allows a provider to suction both right and left bronchi of the lungs as well as the trachea in a controlled and safe manner when a patient is intubated or has a tracheostomy tube.

2. Description of Related Art

Intubated patients develop a pooling of secretions inside the bronchi of the lungs and in the trachea, and require frequent or constant suctioning to remove these secretions. Current processes utilize an unguided, directionless suction catheter which is inserted into an endotracheal tube (ETT) or tracheostomy tube (also known as a "trach") and is simply dropped into the lungs and pulled back slowly while suctioning. Because it is directionless, this existing device is less effective and has a tendency to leave fluid behind in one lung field or both.

Complicating the matter, the left bronchus connects to the trachea at a sharp angle (at about a 40 degree angle); this results in most suction catheters being dropped into the right bronchus (which connects to the trachea at only about a 15 degree angle). This leaves the left bronchus frequently un-suctioned, and if it remains in such a state, secretions can build up and may cause serious complications such as pneumonia or collapse of all or part of a lung field (atelectasis), and these may also propagate to a worsening of acute respiratory distress syndrome (ARDS) and/or septic pneumonia. These complications can require expensive and invasive actions, and prolonged intubation time and costs associated with extended stays in intensive care units of medical facilities such as hospitals.

Examples of existing technology for endotracheal suctioning devices may be found in U.S. Pat. No. 7,191,782, which discloses a suction catheter that may be adapted for removing fluid from a patient from application of negative pressure to a lumen of a tubular portion. Another example may be found in U.S. Pat. No. 5,246,012, which discloses a catheter for performing bronchoalveolar lavage comprising a sampling catheter so sized and configured as to extend from a bronchiole in the lung of a patient through the upper respiratory system. The assembly also includes means for directing the distal end of the sampling catheter into a preselected lung of the patient. Neither of these patents teach a control mechanism or lever for accurately guiding the distal end of the sampling catheter.

Another example of existing attempts to reach both bronchi of the lungs is found in U.S. Patent Publication No. 2011/0313347, which discloses a catheter that includes a distal end adapted to be introduced into the trachea and/or into the bronchi of a patient to suck up fluid secretions or other similar material. The distal end includes a viewing means that includes optical fibers suitable for transferring an image and a micro-camera or another visualization technology, and lighting means that includes other optical fibers suitable for guiding light. These enable the operator to identify the position of the distal end in the trachea and bronchial tree on a screen to ensure that the tube of the catheter is adjacent to or inside collections of fluid secretions. However, there is no mechanism for directional control of the device that allows for greater suctioning capability of the left bronchus.

BRIEF SUMMARY OF THE INVENTION

It is therefore one objective of the present invention to provide a system and method of enabling directional control of a device inserted into the body of an intubated patient. It is another objective of the present invention to provide a system and method of accurately suctioning the left bronchus of an intubated patient using an endotracheal or other similar device.

It is another objective of the present invention to provide a suction catheter that enables guided removal of secretions inside the bronchi, lungs, trachea and other parts of the body. It is yet another objective of the present invention to provide a system and method that reduces incidents of pneumonia, atelectasis, acute respiratory distress syndrome (ARDS), and other complications of re-intubation, unintended extubation, and premature extubation resulting from un-suctioned left bronchi or right bronchi or improperly suctioned trachea. It is still another objective of the present invention to provide a device to the field of medicine that reduces patient intubation time and costs associated with extended stays in the intensive care units of medical facilities.

The present invention is an apparatus that allows the provider to suction both right and left bronchi of the lungs as well as the trachea in a controlled and safe manner. The apparatus is embodied in a bi-lateral endobronchial suctioning device (BESD) that is adapted for articulation through a tube such as an endotracheal tube or trach. The bi-lateral endobronchial suctioning device includes a control lever that allows a user to flex the tip of the device between the left and the right to suction both sides of the lungs. The bi-lateral endobronchial suctioning device therefore enables directional control of what would otherwise be a flimsy suctioning catheter.

The BESD also includes a bronchoalveolar lavage (BAL) port. This port allows sterile saline or other liquids or fluids to travel down the catheter lumen to, for example, assist with breaking up thick secretions which collect in the airways. In prior art devices, solutions such as sterile saline are simply squirted down the endotracheal tube, which gives no directional control over where the solutions are going, nor any intuitive way to remove it. With the BESD and suctioning system of the present invention, solutions such as sterile saline travel directly to the area of the airways that are to be suctioned, under the control of the provider.

Other objects, embodiments, features and advantages of the present invention will become apparent from the following description of the embodiments, taken together with the accompanying drawings, which illustrate, by way of example, the principles of the invention.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 3A is a perspective view of a bi-lateral endobronchial suctioning device according to the present invention;

FIG. 3B is an enlarged perspective view of a controller end of a bi-lateral endobronchial suctioning device according to the present invention;

FIG. 4 is one side view of a bi-lateral endobronchial suctioning device according to the present invention;

FIG. 5 is another side view of a bi-lateral endobronchial suctioning device according to the present invention;

FIG. 6 is a side view of a bi-lateral endobronchial suctioning device, with an articulating tip directed to one side using a control mechanism according to the present invention;

FIG. 7 is a side view of a bi-lateral endobronchial suctioning device with an articulating tip directed to a second side from that shown in FIG. 6 using a control mechanism according to the present invention;

FIG. 15 is a diagram of a bi-lateral endobronchial suctioning device showing a flow of fluids out of the device upon actuating a button according to one embodiment of the present invention;

FIG. 16 is a diagram of a bi-lateral endobronchial suctioning device showing a flow of fluids into the device with the use of a bronchoalveolar lavage (BAL) port according to one embodiment of the present invention;

FIG. 26 is an isometric exploded view of an alternative embodiment of the controller end.

Figure 1:
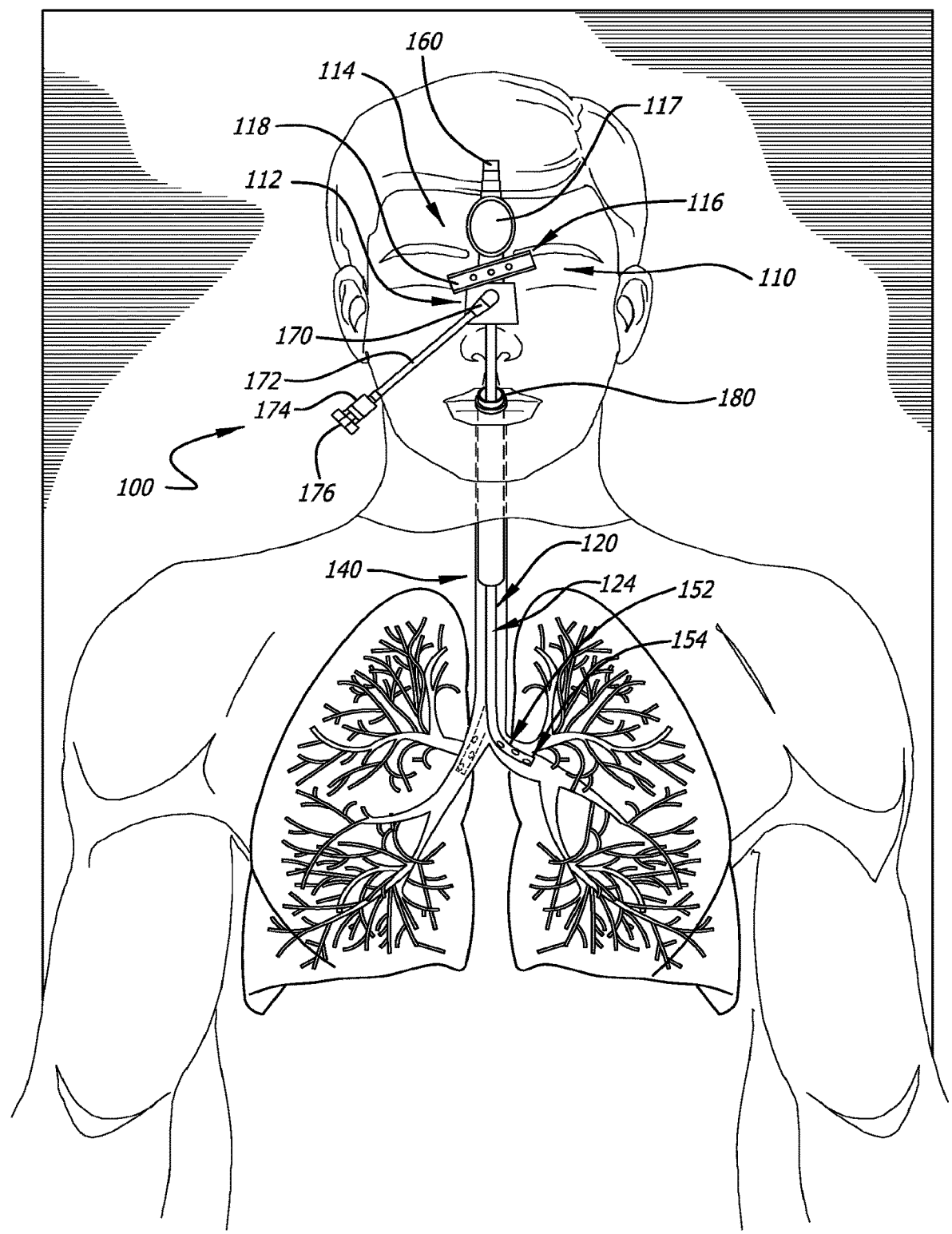
FIG. 1 is a frontal view of an intubated patient using a bi-lateral endobronchial suctioning device according to the present invention.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
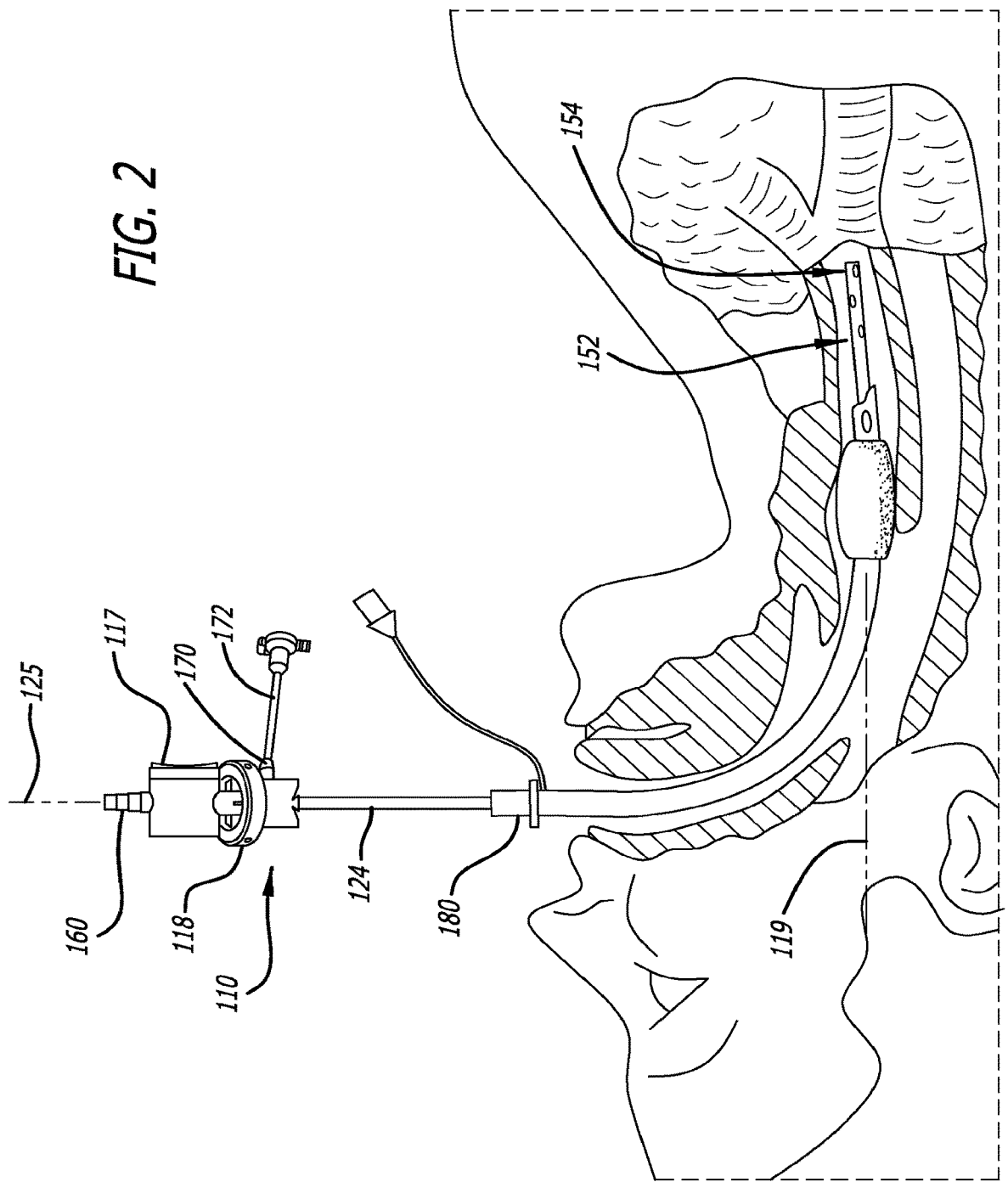
FIG. 2 is a side view of an intubated patient using a bi-lateral endobronchial suctioning device according to the present invention.

The present invention discloses a system and method of medical suctioning, in a bi-lateral endobronchial suctioning device and apparatus (BESD) 100 that is configured to enable a physician or other provider to suction both right and left bronchi of a patient's lungs in a controlled and safe manner when the patient is intubated. FIG. 1 and FIG. 2 show frontal and side views of the present invention while being deployed on an intubated patient.

The BESD 100 includes a control portion 110 that comprises a control interface 112 at a controller (or top) end 114. The control interface 112 is used to manipulate a control mechanism 116 that actuates one or more cables 122 within a catheter suctioning portion system 120. The one or more cables 122 are disposed within or around a lumen, or shaft, 126 of a catheter 124. The catheter suctioning portion and system 120 also include one or more tubes 146 that together form the catheter 124. The one or more cables 122 enable a provider to maneuver and manipulate a tip 152 of an articulation portion 150 at a distal bottom end 154 of the BESD 100. FIG. 3A is a perspective view of the bi-lateral endobronchial suctioning device according to one embodiment of the present invention, and FIG. 3B is an enlarged perspective view of a controller end of a bi-lateral endobronchial suctioning device. FIG. 4 and FIG. 5 show side views of the bi-lateral endobronchial suctioning device.

The control mechanism 116 enables a provider to flex the articulating tip 152 of the articulation portion 150 in multiple directions to enable suctioning of both sides of the lungs of an intubated patient. This allows for directional control of the suctioning catheter system 120. A button 117 on the control mechanism 116 allows the provider to initiate and terminate bronchial or other suctioning with the BESD 100 once the control mechanism 116 has been actuated to maneuver the articulating tip 152 as desired in the lungs or trachea. A suction nozzle 160 is positioned at the controller end 114 for attachment to an external device into which fluids or secretions are to be suctioned from the patient using the BESD 100. The BESD also includes a bronchoalveolar lavage (BAL) port 170 coupled to the catheter suctioning portion 120.

The BESD 100 is configured so as to be insertable for use with an endotracheal tube 180 or similar device. A provider inserts the catheter 124 into the endotracheal tube 180, and then uses the top control interface 112 to articulate the tip 152 at the distal bottom end 154.

The top control interface 112 at the controller or top end 114 includes several components configured to actuate the articulating tip 152 via the articulation portion 150 at the bottom distal end 154. The control mechanism 116 is one such component, which in one embodiment is a circular disk 118 with a hollow center so as to form a ring which surrounds an upper portion of the BESD 100 at or near the top end 114. The circular disk 118 is positioned near, and in one embodiment sits just below from, where the button 117 is located. The circular disk 118 has components which couple to the BESD 100 at the upper portion in different configurations, as noted below.

The disk 118 is manipulated by the provider in an up or down manner substantially consistent with a longitudinal plane 125 in which the catheter 124 and the BESD 100 itself lie, as shown in FIG. 6 and FIG. 7. The disk 118 may also be configured to move in rocking manner at slight angles to this up or down movement relative the longitudinal plane 125.

The circular disk 118 of the BESD 100 is therefore also configured to move angularly relative to its own horizontal axis. The circular disk 118 is capable of pivoting, or rocking up or down, depending on which direction the provider wants an articulation of the distal bottom end 154 of the BESD 100 to be directed. The top control interface 112 therefore include means for enabling this up, down, and angular movement of the circular disk 118.

The control mechanism 116 includes actuation components, such as a pin 191 in a center portion 192 thereof, running through the horizontal axis relative to the shape of the circular disk 118 and connecting the control mechanism 116 to the rest of the suction catheter portion 120. This pin 191 acts as a fulcrum for the angular movement of the circular disk 118. The pin 191 may run through the catheter 124 at or near the top end 114, but in other embodiments, the pin 191 may be configured so that it does not penetrate all the way through, as the catheter 124 itself may block passage of the pin 191. The circular disk 118 may also include two additional pins 193 which run along the same axis and are on opposite sides of the main fulcrum pin 191. The additional pins 193 allow one or more wires 194 (not shown) forming the cables 122 to flex, which drives the depth of articulation at the articulating tip 152 at distal bottom end 154.

Figure 17:
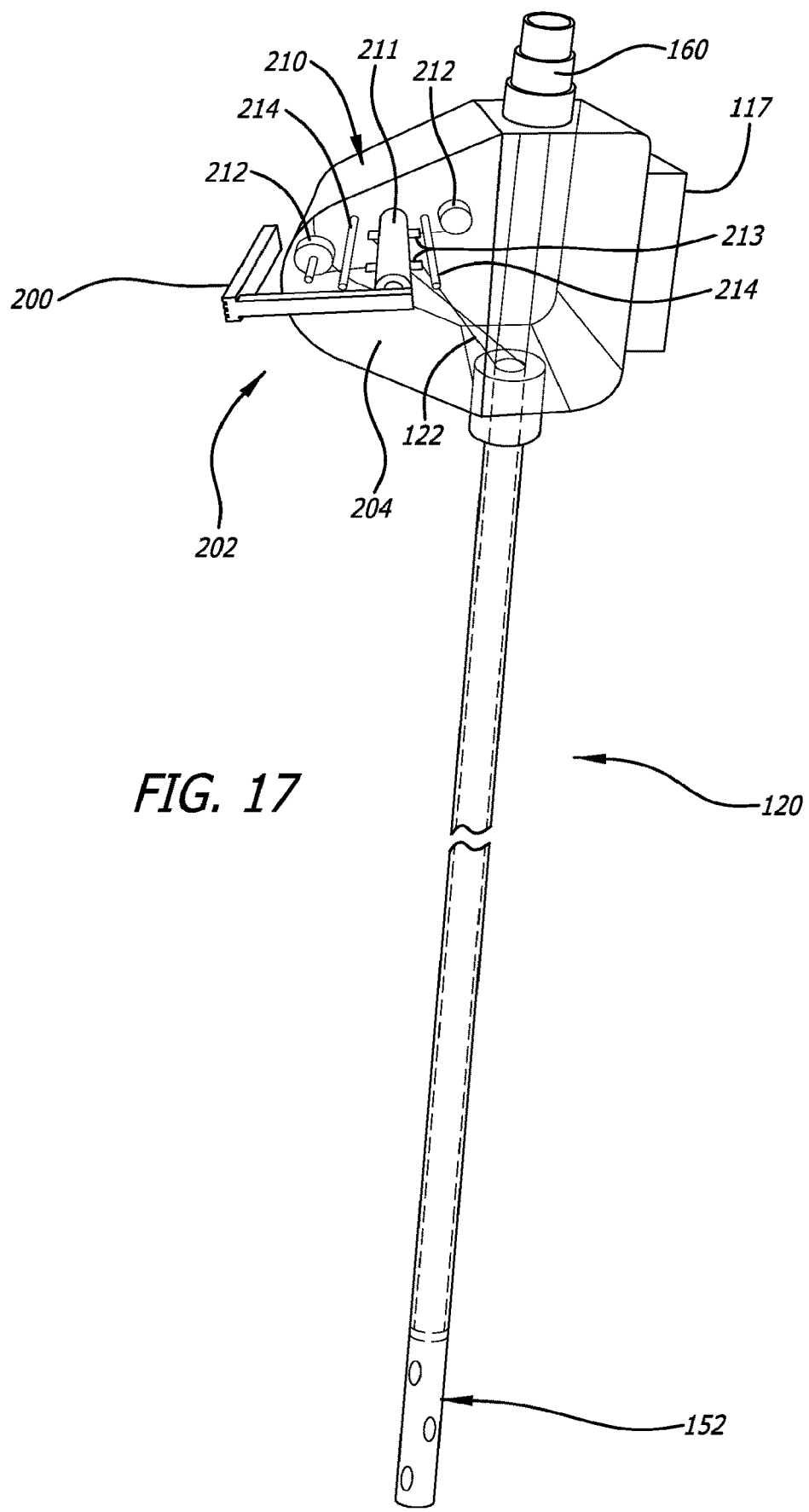
FIG. 17 is a perspective view of interface components of a bi-lateral endobronchial suctioning device according to another embodiment of the present invention.
Figure 18:
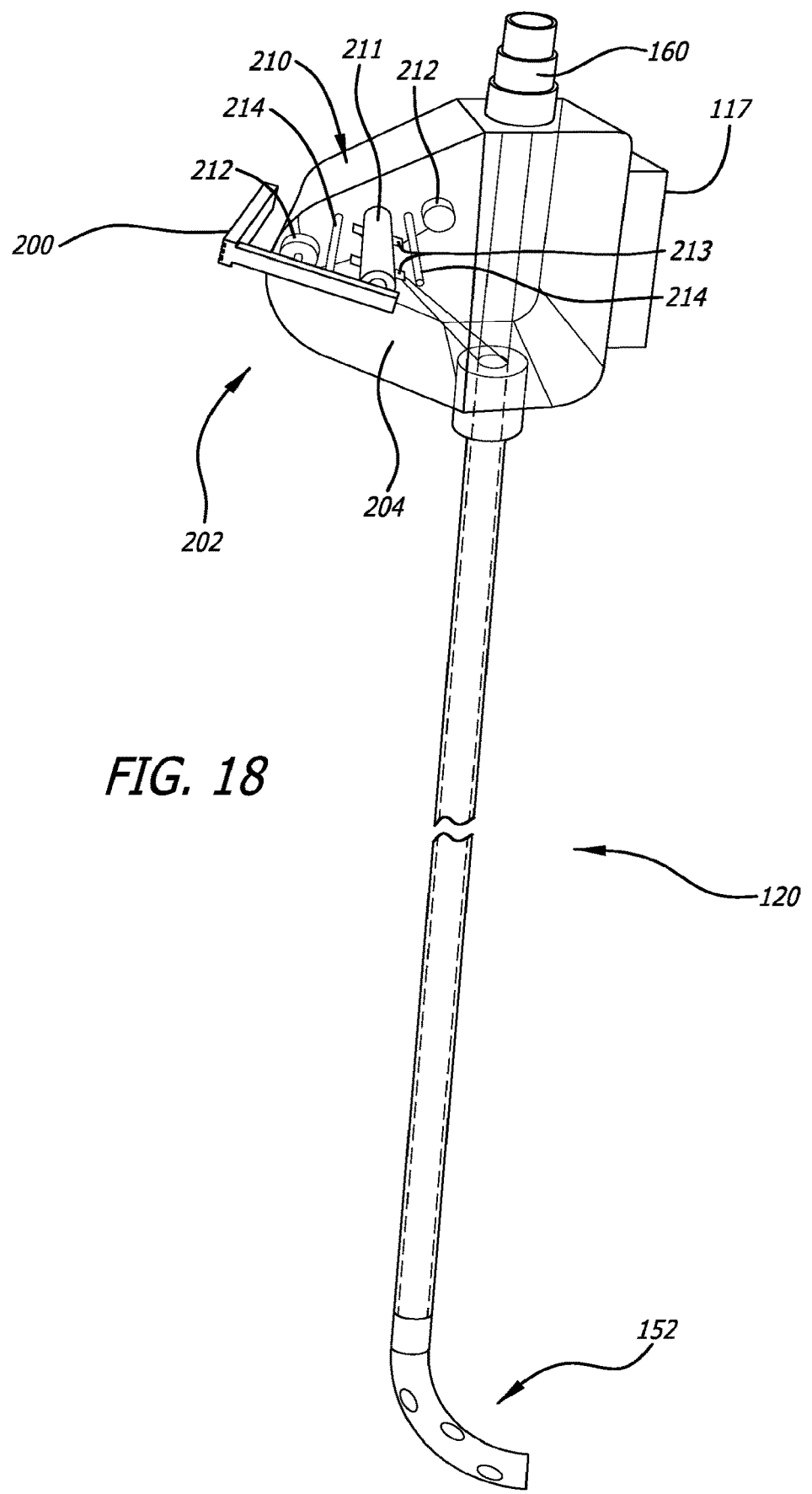
FIG. 18 is a perspective view of interface components of a bi-lateral endobronchial suctioning device articulating a distal tip to one side according to the embodiment of FIG. 17.
Figure 19:
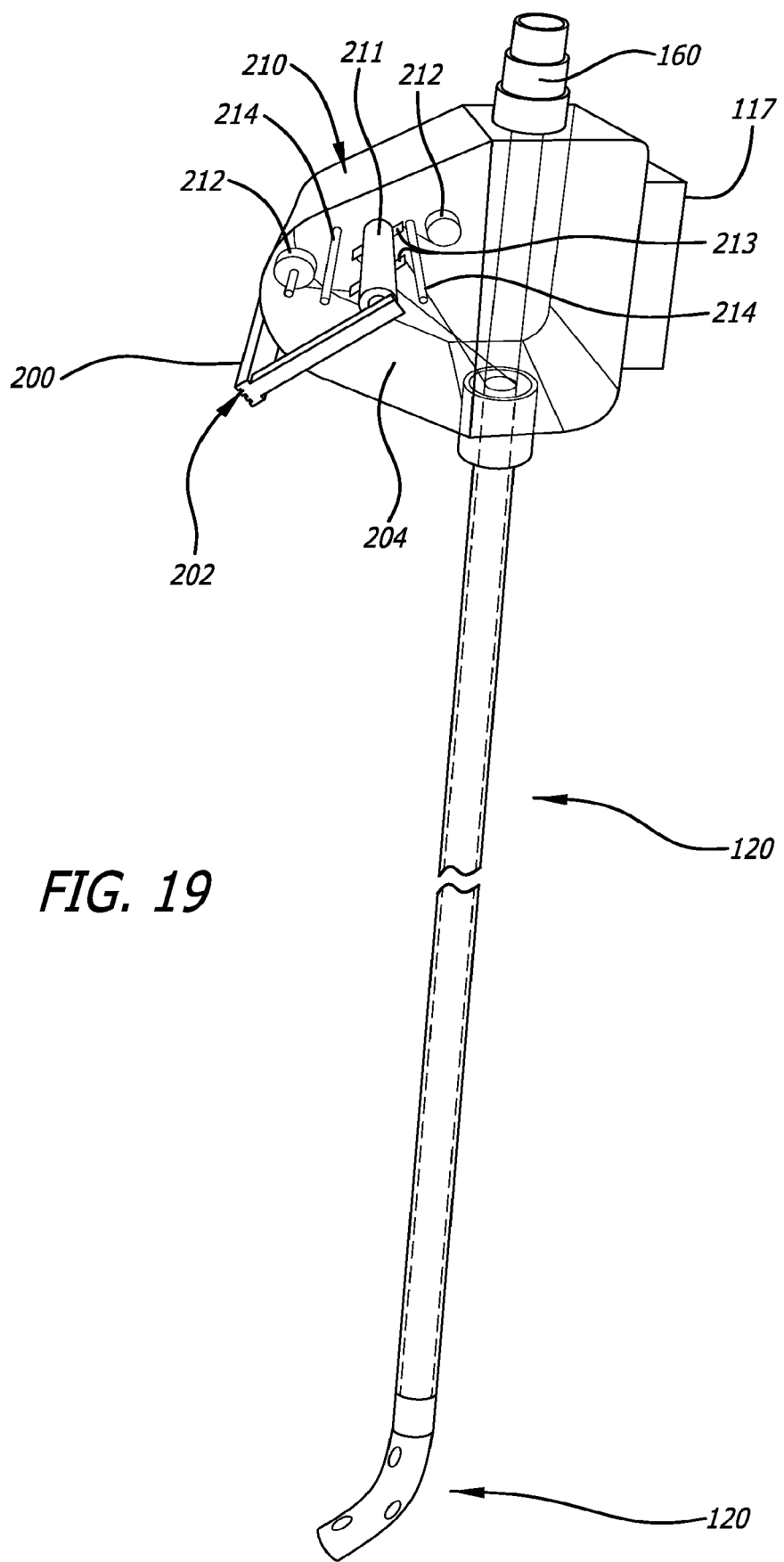
FIG. 19 is a perspective view of interface components of a bi-lateral endobronchial suctioning device articulating a distal tip to another according to the embodiment of FIG. 18.

In one embodiment of the present invention, the control mechanism 116 may comprise a control lever 200 and a cylindrically-shaped housing 202 that is the structure holding all of the components 210 actuated by the control lever 200. The control lever 200 is actionable from an outside 204 of the housing 202, and can be either depressed or elevated to cause articulation of the articulating tip 152 at the distal bottom end 154 of the suction catheter 124. FIG. 17 shows this embodiment of the BESD 100, and FIG. 18 and FIG. 19 demonstrate the actuation of the control lever 200 and the articulation of the distal bottom end 154 to either side.

Inside the housing 202 are the actuation components 210 which work in synchronicity with the control lever 200 to cause the distal tip articulation 152 according to this embodiment. One actuation component 210 is a rod 211 which the control lever 200 attaches to, and which turns clockwise or counter-clockwise depending on which direction the control lever 200 is elevated or depressed respectively by the provider. The rod 211 has two small holes which are elongated horizontally in relation to the suction catheter system 120. The one or more cables 122, which attached to the distal articulating tip 152 of the suction catheter 124, run along the sides of the suction catheter 124 on opposing sides, enter the housing 202, and pass through the small holes in the rod 211. The holes allow torque to occur in order to cause articulation of the distal articulating tip 152. Each cable 122 is re-oriented 90 degrees as it enters the housing 202 of the BESD 100 before entering the elongated holes in the rod 211. After passing through the holes, they couple to a small coil spring 212 on either side. This configuration allows the cables 122 to have some flexibility when the control lever 200 is not actuated. As the control lever 200 is elevated or depressed by the provider, the cables 122 begins to wind around the rod 211, so that one cable 122 tightens and the other loosens. This translates into a pull/loosening motion at the distal articulating tip 152 of the suction catheter where the string/cables attach.

As noted above the coil springs 212 are disposed on opposing sides of the rod 211, which also may include two dowels 213 perpendicularly inserted in the holes in the rod 211 in another embodiment of the present invention. Two wire guide cylinders 214 are positioned parallel to the rod 211, and each cable 122 passes through a wire guide cylinder 214, and a dowel 213 so that the cable 122 passes perpendicularly through the holes in the rod 211, guided by the wire guide cylinder 214. Upon exiting each dowel 213, the cables 122 extend and are inserted into the catheter 124 on opposing sides thereof. In a further alternative embodiment, a cable 122 is simply attached to the rod 211 at some point, either at a vertical cross-beam attached to the rod 211 or simply wrapped around the rod 211 only in order to allow the desired articulating depth.

Figure 8:
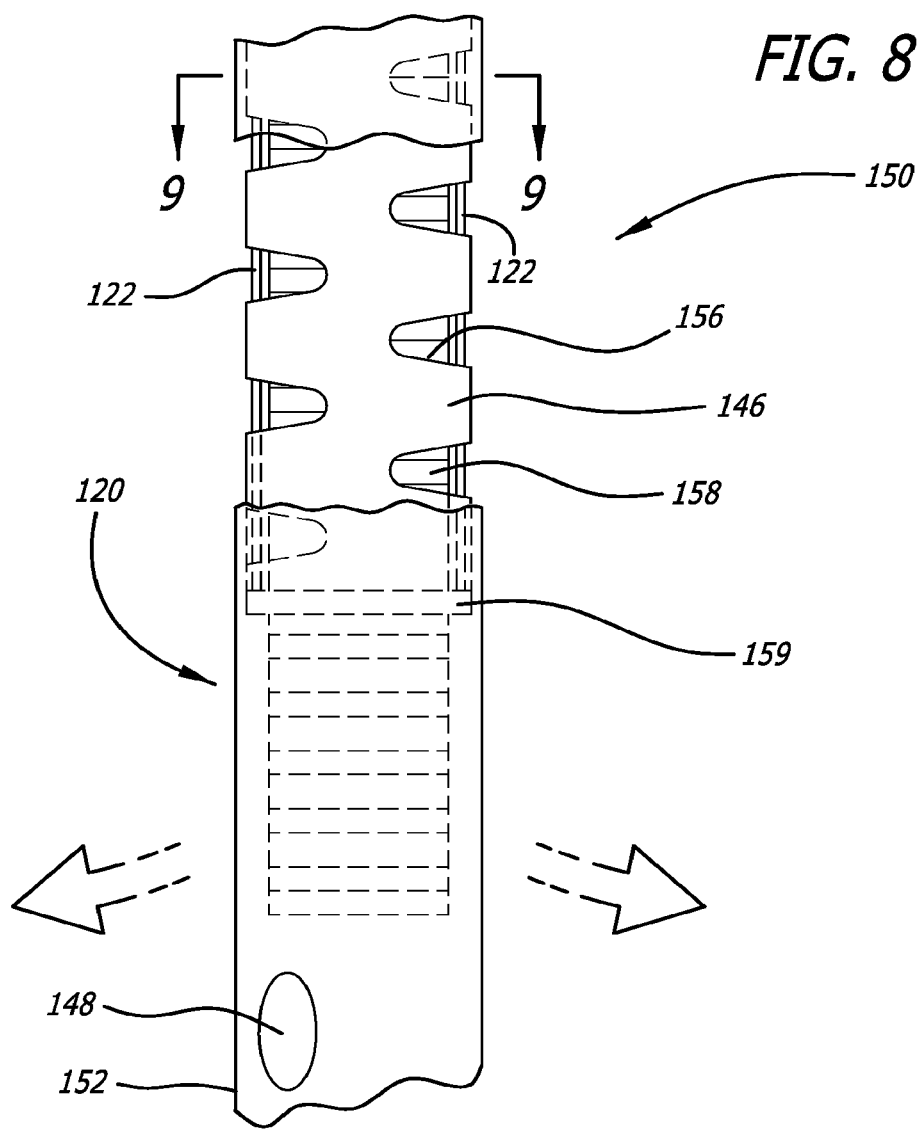
FIG. 8 is a close-up view of a catheter portion and articulating section of a bi-lateral endobronchial suctioning device according to one embodiment of the present invention.
Figure 9:
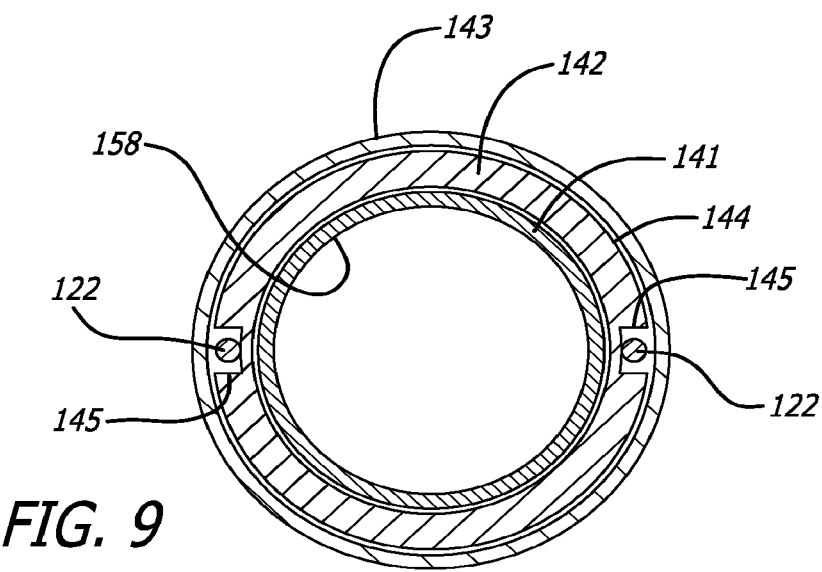
FIG. 9 is a cross-sectional view of the catheter portion of FIG. 8.
Figure 10:
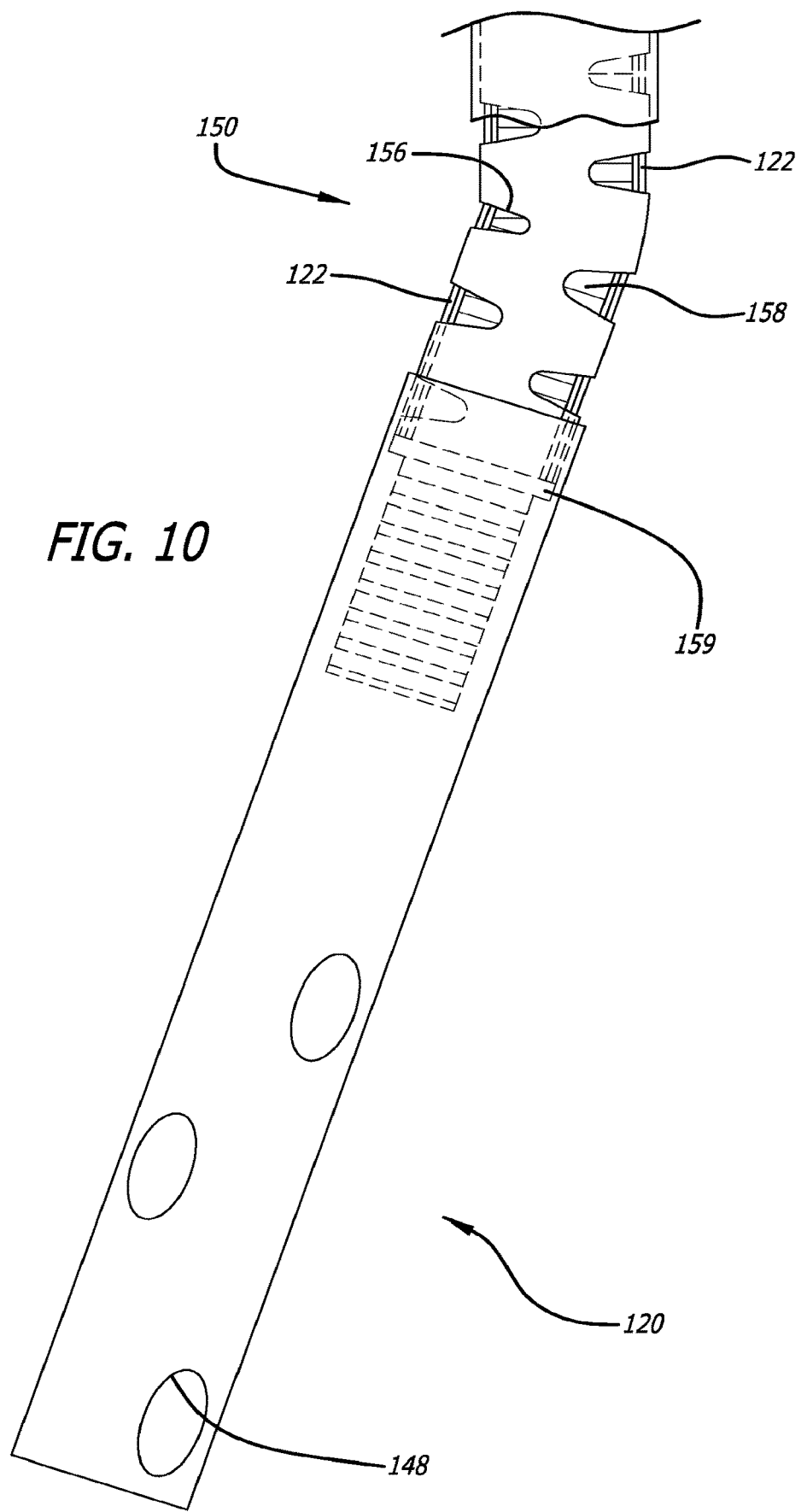
FIG. 10 is a view of a catheter portion articulated to one side according to the embodiment of FIG. 8.
Figure 11:
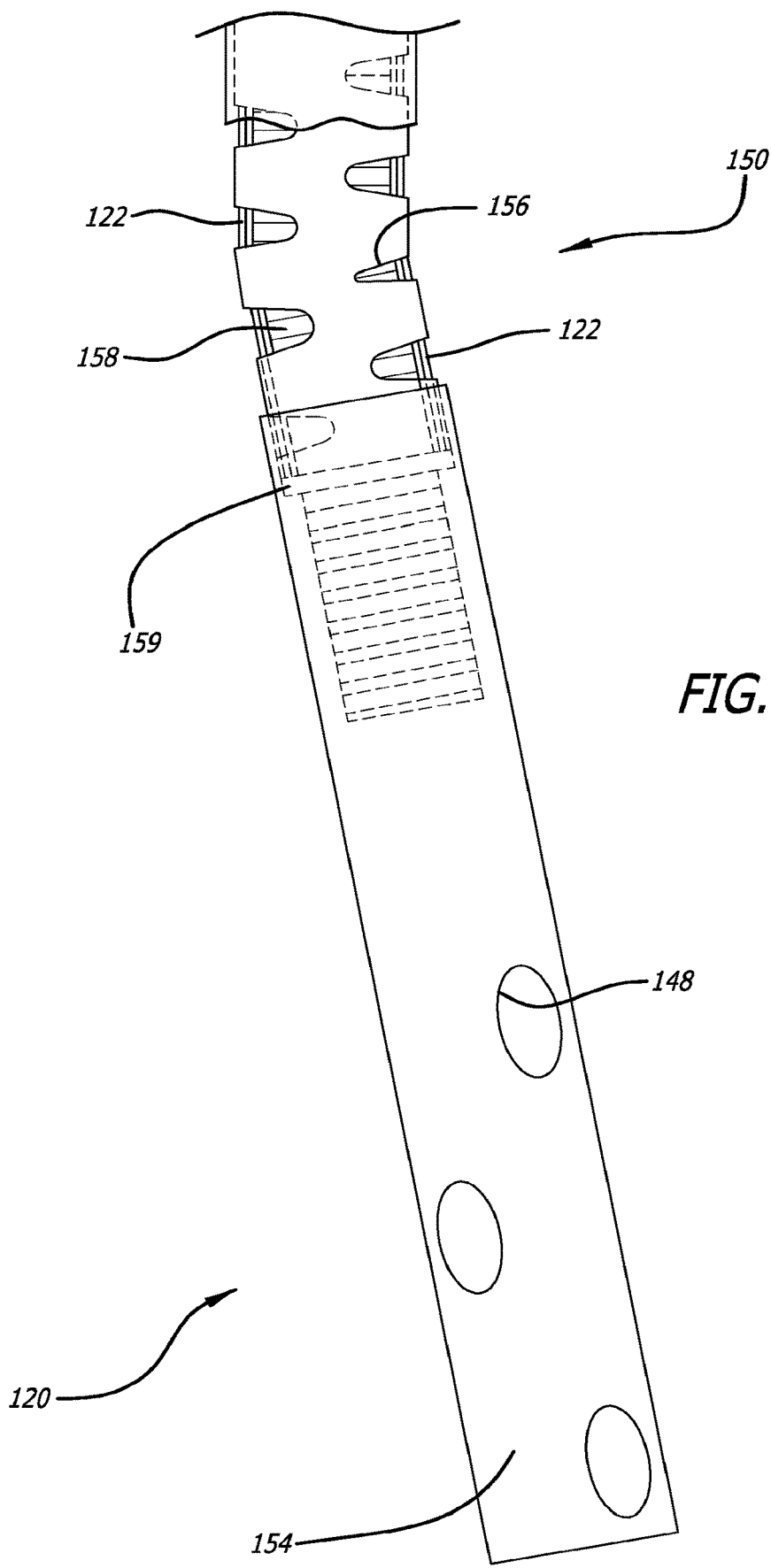
FIG. 11 is a view of a catheter portion articulated to another side from that of FIG. 10, according to the embodiment of FIG. 8.

FIG. 8 through FIG. 11 are various views of a catheter 124 of the BESD 100 according to one embodiment of the present invention. FIG. 8 is a close-up of the one or more tubes 140, and FIG. 9 is a cross-sectional view of the tubes 140. FIG. 10 and FIG. 11 show the catheter 124 articulated to different sides by the control mechanism 116.

The one or more tubes 140 that together form at least a substantial portion of the catheter 124 may include an inner tube 141, a middle tube 142, and an outer tube 143. Regardless of the embodiment, it is contemplated there are multiple layers of catheter tubing, with a cable 122 running either in between or through them. This forms a "catheter inside a catheter" appearance as in FIG. 8. Where there are three tubes, they form a three-ply catheter arrangement, with the outer-most layer forming a layer or sheath extending all the way from top to bottom of the catheter 124. One embodiment will be just one catheter tube with 3 holes one hole for section and two smaller holes on opposite ends where the cables run through. In that embodiment there would be no multi-ply catheters.

In one embodiment, the cables 122 are positioned within the lumen 126 of the catheter 124 to run along an outer surface 144 of a middle tube 142, between the middle tube 142 and the outer tube 143. The cables 122 may be positioned to run along a plurality of grooves, channels, or recesses, 145 in the outer surface 144 to keep them in place as they run along the outer surface 144. The grooves, channels, or recesses 145 may extend along a significant portion of the outer surface 144 of the middle tube 142, or may be periodically situated thereon. Holes may also be positioned within walls of the catheter 124 for the cables 122 to pass through.

The BESD 100 includes an articulation joint portion 150, which enables the catheter 124 to be actuated to move the articulating tip 152 at the distal bottom end 154 as needed. Several manifestations of this articulation joint portion 150 are contemplated, and are within the scope of the present invention. For example, in one embodiment of the present invention, one or more "nicks" or grooves 156 are made in one or more of the tubes 140 forming the catheter 124 to allow the tube 140 to bend where those nicks 156 are positioned. As shown in FIG. 8, FIG. 10, and FIG. 11, these nicks/grooves 156 are on the middle tube 142, with the outer tube 143 forming a sheath over the middle tube 142. A spring coil 158 may or may not form at least a part of the inner tube 141 and runs along an inside surface 147 of the catheter lumen 126 and near to where the nicks and grooves 156 are positioned in the catheter 124, which imparts strength to the catheter 124 and to help spring the catheter 124 back to its original form when the provider ceases actuating the control mechanism 116.

Figure 12:
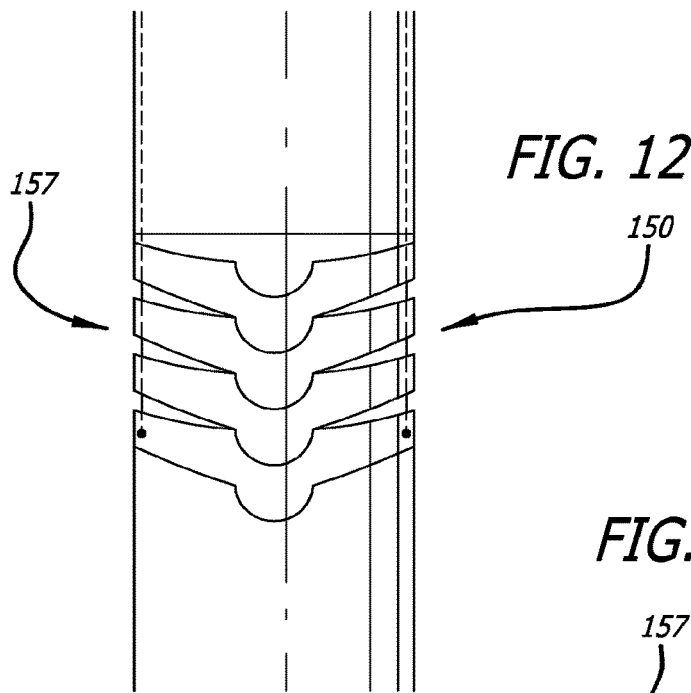
FIG. 12 is a close-up view of articulation components of a catheter portion of a bi-lateral endobronchial suctioning device according to another embodiment of the present invention.
Figure 13:
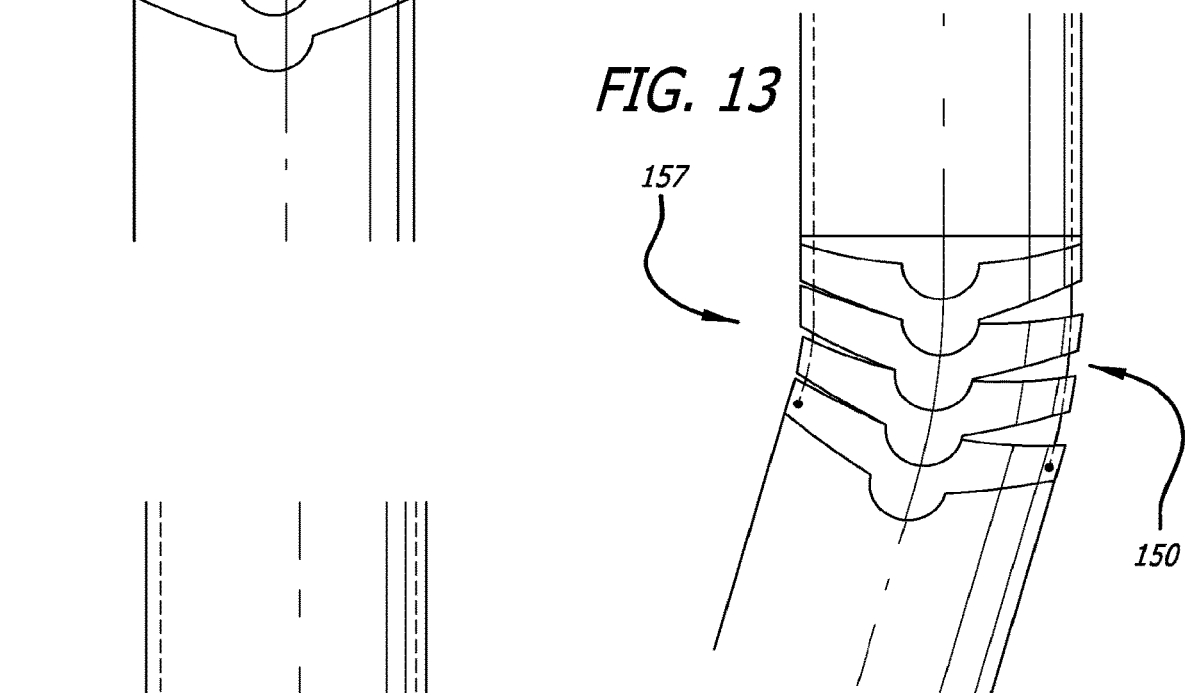
FIG. 13 is a close-up view of articulation components of a catheter portion of a bi-lateral endobronchial suctioning device with the catheter angularly articulated according to the embodiment of FIG. 12.
Figure 14:
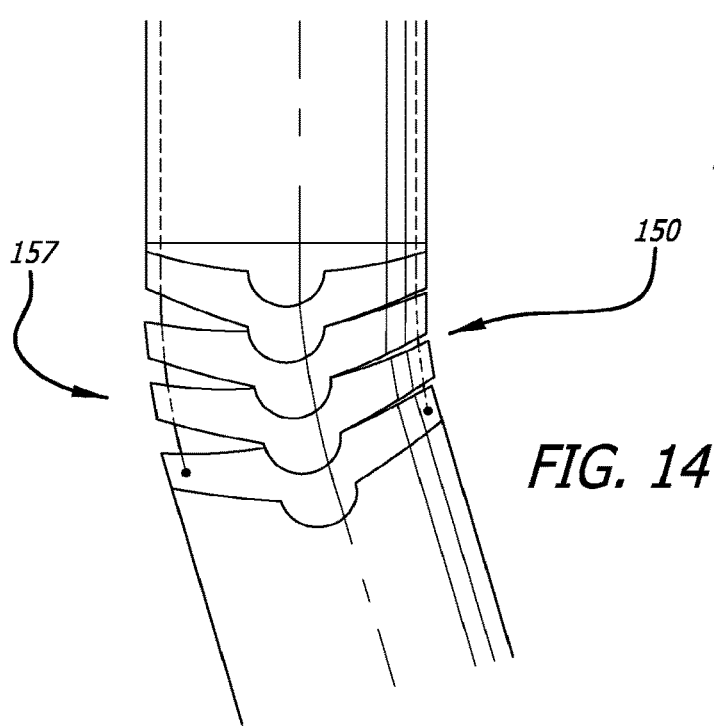
FIG. 14 is another close-up view of articulation components of a catheter portion of a bi-lateral endobronchial suctioning device with the catheter angularly articulated according to the embodiment of FIG. 12.

FIG. 12, FIG. 13, and FIG. 14 show an alternative embodiment, in which the articulation joint portion 150 comprises a plurality of fitted articulation pieces 157 forming part of the middle tube 142. In this embodiment, the cables 122 run through the fitted articulation pieces 157 along holes or grooves in the outer surface of the middle tube 142. The plurality of fitted articulation pieces 157 are form-fitting relative to each other, and perform a rocking movement when the control mechanism 116 is actuated, causing articulation to occur in the articulating tip 152 at the distal bottom end 154. The fitted articulation pieces 157 may also have grooves 156 between them which allow them a greater degree of movement. The cables 122 end at the last fitted articulation piece 157. In still another alternative embodiment, the catheter 124 may include just a spring forming at least a part of the inner tube 141, with no nicks or grooves 156 in the middle tube 142. In still another embodiment, the inner 141 tube acts as a spring and only extends so far as to span the articulating joint portion 150 itself. In yet another embodiment the articulating joint consists of one single coupler where the cables attach as well as a main catheter and a softer durometer distal catheter tip.

Other features of the present invention are also contemplated. For example, the outer tube 143 may include one or more orifices 148 on the surface thereof, and at or near the bottom distal end 154, to enable suctioning through the catheter 124. These orifices 148 are shown for example in FIG. 3A, FIG. 4, FIG. 5, FIG. 6, FIG. 7, FIG. 10, FIG. 11, and in FIGS. 15-19. In another embodiment, the articulation joint portion 150 may also include a ring 159 positioned roughly a few centimeters up along the catheter 124 from the terminus of the distal bottom end 154. The one or more cables 122 are coupled to, and end at, this ring 159, which is rotatable when the provider actuates the control mechanism 116 to articulate the articulating tip 152. The ring 159 is positioned at a point along a length of the catheter 124, referenced from the top controller end 114, to where the middle tube 142 ends, and the one or more nicks or grooves 156 also end, to anchor the one or more cables 122 within the catheter 124.

Referring to FIG. 1, FIG. 2, FIG. 3A and FIG. 3B, and as noted above, the BESD 100 also includes a bronchoalveolar lavage port (BAL) port 170 that allows fluids, solutions, or medications, such as for example sterile saline, to travel down the catheter 124 in order to assist with breaking up thick secretions which collect in the airways of intubated patients. The BAL port 170 may be located at various positions along the catheter 124, such as for example near the top control interface 112 and near to where the control mechanism is actuated, which is where a provider's hands would be placed when operating the BESD 100.

Without a BESD 100, sterile saline is simply squirted down an endotracheal device, which provides no directionality to where the sterile saline is going. However, with the directional capability of the BESD 100 of the present invention, the BAL port 170 enables sterile saline to go directly to the area of the airways that are to be suctioned. The BAL port 170 therefore communicates with the main suction catheter 124 to allow fluids such as saline to go into a specific area, wherever the distal bottom end 154 of the main suction catheter 124 lies. FIG. 16 shows the flow of fluids into the BESD 100 using the BAL port 170.

In one embodiment, the BAL port includes a small tubular extension 172, with a cap 176 on an end 174 of the tubular extension 172. The cap 176 prevents air from escaping while suctioning, and together the extension 172 and cap 176 operate to keep the BESD 100 a closed system. The cap 176 may be removed after the BESD 100 has been deployed into a patient's lung, and a syringe can be attached to the tubular extension 172 so that saline can be squirted down the catheter 124 through the BAL port 170. The extension 172 communicates with the main catheter 124 so that when saline enters the BAL port 170 it also enters the catheter 124, it flows into the lung. The provider then closes the cap 176 and begins suctioning out the lung that now has that saline in it with the BESD 100.

Figure 20:
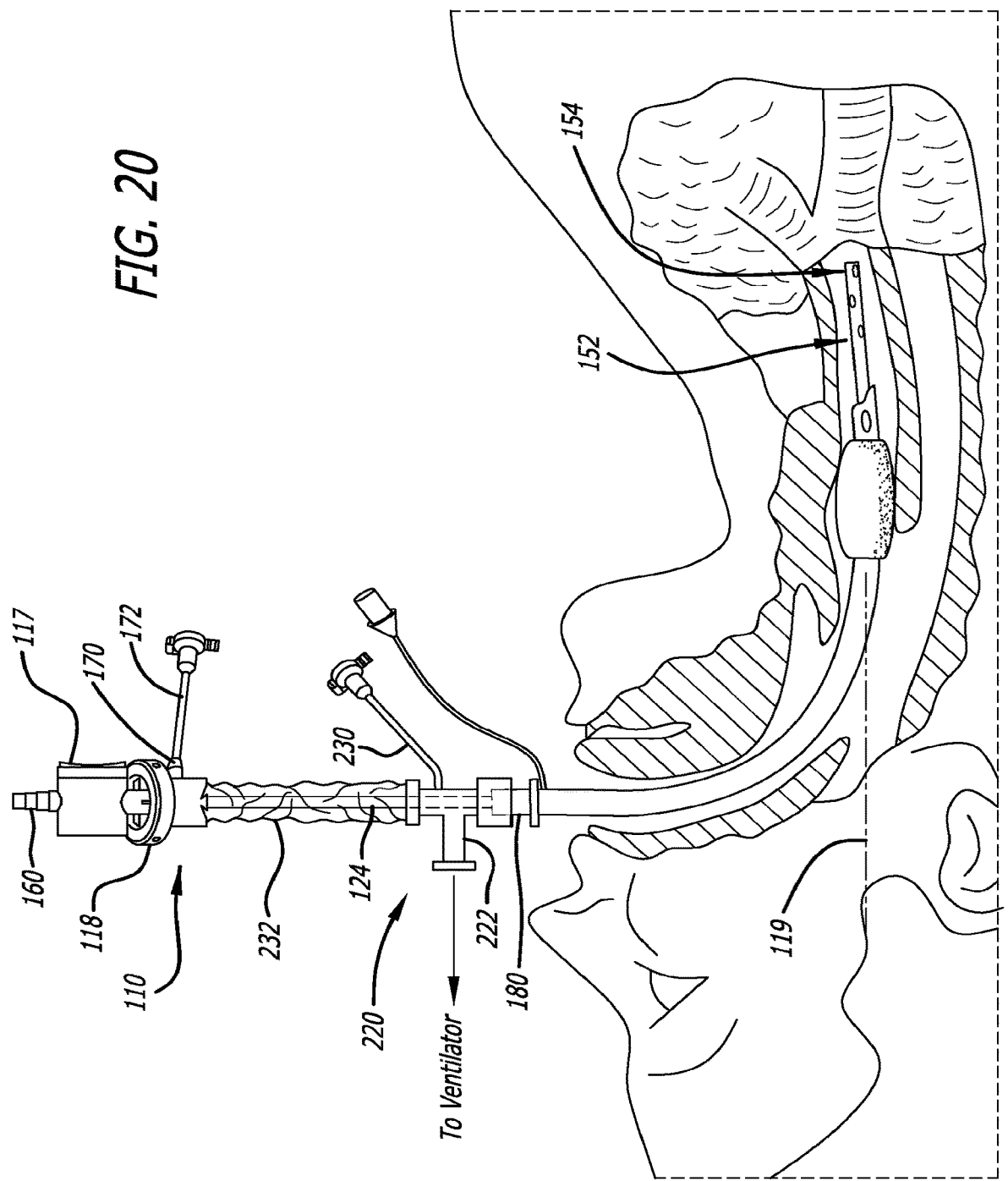
FIG. 20 is another side view of an intubated patient using a bi-lateral endobronchial suctioning device according to another embodiment of the present invention.
Figure 21:
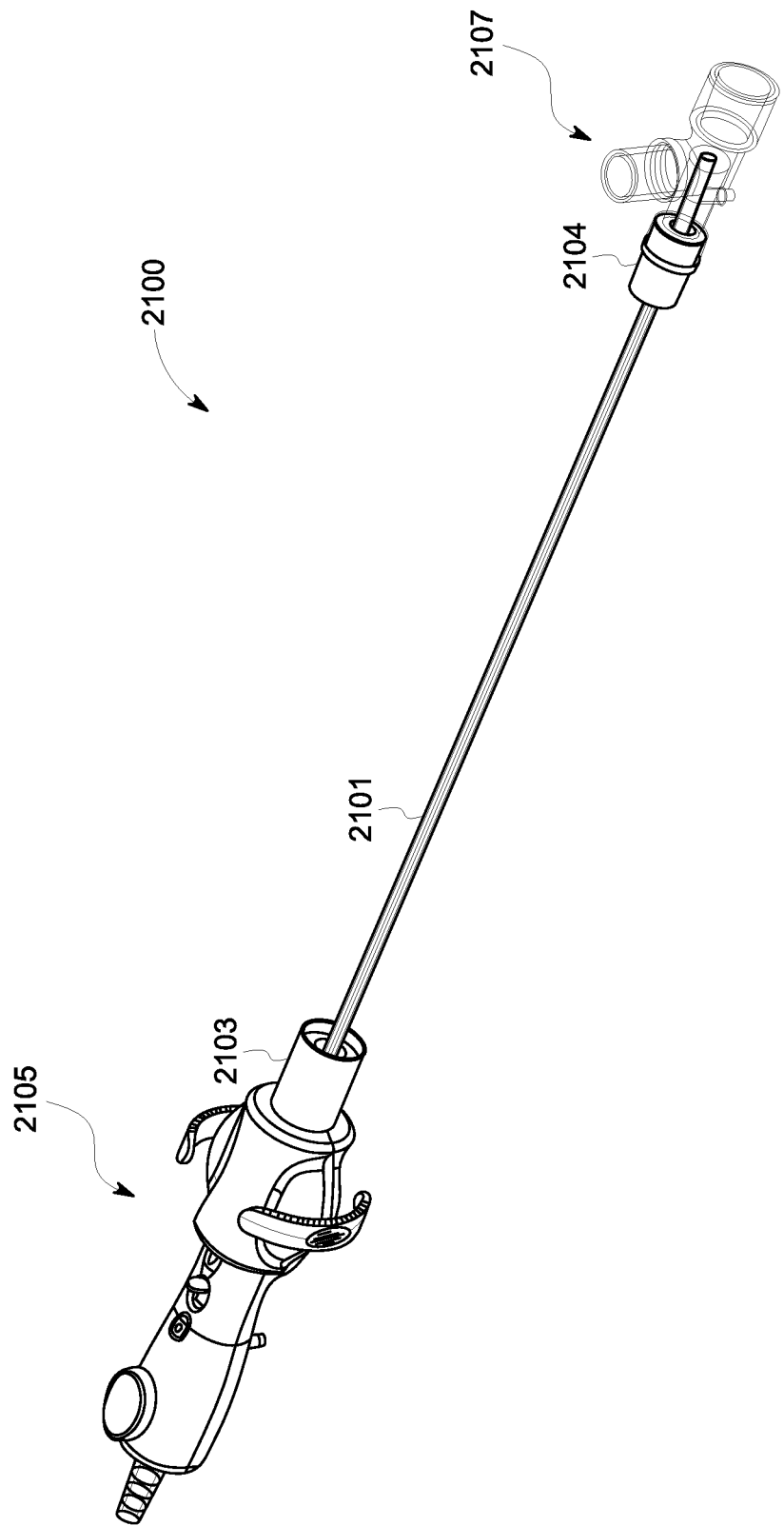
FIG. 21 is an isometric view of an endobronchial suctioning device in accordance with an alternative embodiment of the present application.

Referring to FIG. 20, the BESD 100 may also include a manifold 220 that provides a means of attachment to a ventilator machine, to the end of an endotracheal tube 180, and to a catheter cleaning and irrigation system 230. The manifold 220 therefore acts as a means to keep the patient on a ventilator while at the same time giving the provider the ability to suction the patient. The catheter cleaning and irrigation system includes a cleaning catheter 230 and also includes a sterile sleeve which keeps the catheter 124 sterile while it is not being deployed into the patient. A port 222 at the attachment point of the manifold 220 to the BESD 100 may be provided to couple the BESD 100 to a ventilator machine. Such a "BAL like" port 222 is not to be confused with an actual BAL port 170, because it is not used for bronchoalveolar lavage. If a clean, new suction catheter 124 is needed, the BESD 100 may be detached from the manifold 220 and a new BESD 100 may be re-attached. This attachment point therefore forms a chamber where the catheter cleaning and irrigation system attaches.

In one additional embodiment of the present invention, the manifold 220 may be a separable component from the suction catheter portion 120, so that the two can be disconnected from each other at an attachment point. A cap may also be included to cover the entrance to the manifold when not coupled to the suction catheter portion 120. In another embodiment, the catheter components are not detachable from the manifold 220, so that together they form a single unit. A housing may be used to connect to the manifold 220 for the purposes of guiding the suction catheter down the endotracheal tube 180. Regardless, it is to be understood that the BESD 100 may be designed where it is permanently attached to a manifold 220 or removably attached to a manifold 220, so that a chamber is formed to which a separate catheter cleaning and irrigation system or ventilator may be attachable to the entire BESD 100.

As noted above, the BESD 100 includes a suctioning system which enables it to suction secretions from an intubated patient's lung. This suctioning system includes, in addition to the catheter 124, a button 117 at the interface portion 112 near the top end 114, and a suction nozzle 160 through which secretions or fluids from the left and right bronchi of an intubated patient exit the BESD 100.

FIG. 15 is a diagram of the bi-lateral endo bronchial suctioning device showing a flow of fluids out of the BESD 100 upon actuating the button 117. The button 117 therefore acts as a toggle to allow the provider to initiate and terminate suctioning using the BESD 100. It is contemplated that such initiating and terminating suctioning may be performed by other components, such as a switch or a lever, and therefore button 117 is but one of many styles and shapes of components which may be used to actuate suctioning in the BESD 100.

The BESD 100 may also include one or more components that enable connection and use with systems and devices such as an ultrasound machine, for example on a patient's chest, to locate the tip of the catheter 124 inside a lung field. The BESD 100 may therefore include a hyperechoic component in the articulating tip 152 of the suction catheter 124, so that an ultrasound probe could easily detect and see the articulating tip 152. One example of a hyperechoic component may be one or more thin metal strips or pieces embedded or otherwise located inside the articulating tip 152 at the distal bottom end 154 of the catheter 124 to cause it to be hyperechoic. In another embodiment, the articulating tip 152 may include an anode, and small sensors may be placed on the chest wall of the patient, for example near the nipples, so that when the catheter 124 is close to one of the sensors, a light or other indicator is activated to show that the catheter 124 is in the left or right bronchus. Such a configuration enables certainty as to which bronchus of the lung the catheter 124 is located and aids in articulating the BESD 100.

As indicated above, the BESD 100 may therefore also be configured for use with an ultrasound machine in the field of pulmonology. The catheter 124 in this embodiment may be utilized with ultrasound technology to locate and biopsy lung tumors, with the ultrasound device enabling a determination of which lung field the catheter 124 of the BESD 100 has been articulated in.

The present invention may also include a method of removing built-up secretions in the lungs or other areas of an intubated patient. The method utilizes a device 100 configured for bilateral insertion into an intubated patient's lungs, and includes actuating a control mechanism 116 on the device to manipulate a plurality of cables 122 from a controller end 114 that pass through a catheter portion 120, and articulating a joint portion 150 in the catheter portion 120 so that angular movement of the control mechanism 116 flexes an articulating tip portion 152 at a distal end 154 opposite the controller end 114 into both a left bronchus and a right bronchus of the intubated patient's lungs as desired. The method also includes suctioning the patient's lungs by actuating components to initiate and terminate the removal of bronchial secretions from the intubated patient.

In FIGS. 21-27, an alternative embodiment of an endobronchial suctioning device 2100 in accordance with the present application is shown. It should be appreciated that the features discussed above can be implemented into device 2100, wherein device 2100 can engage with a top for endotracheal use.

Device 2100 includes a catheter 2101 through which articulating cables are disposed as discussed above. The catheter 2101 extends from a first attachment mechanism 2103 to a second attachment point 2104. In this embodiment, a control end 2105 is in communication with catheter 2101 via attachment mechanism 2103 and an endotracheal tube connector 2107 is attached at 2104. It should be appreciated that the control end 2105 provides for a means for the user to manipulate the cables that are extending through the catheter.

Figure 22A:
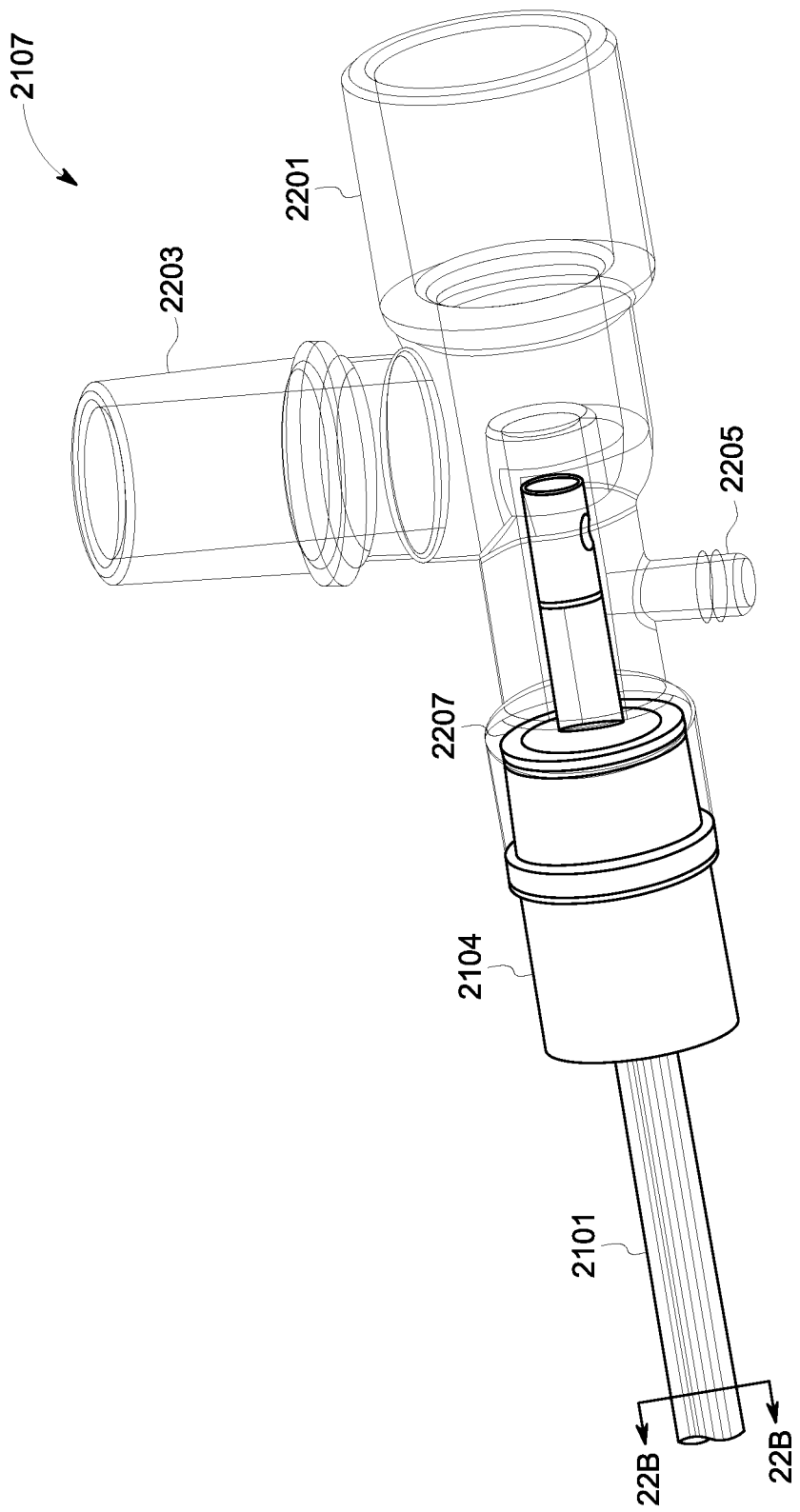
FIG. 22A is an isometric view of an endotracheal tube connector end of the endobronchial suctioning device of FIG. 21.
Figure 23:
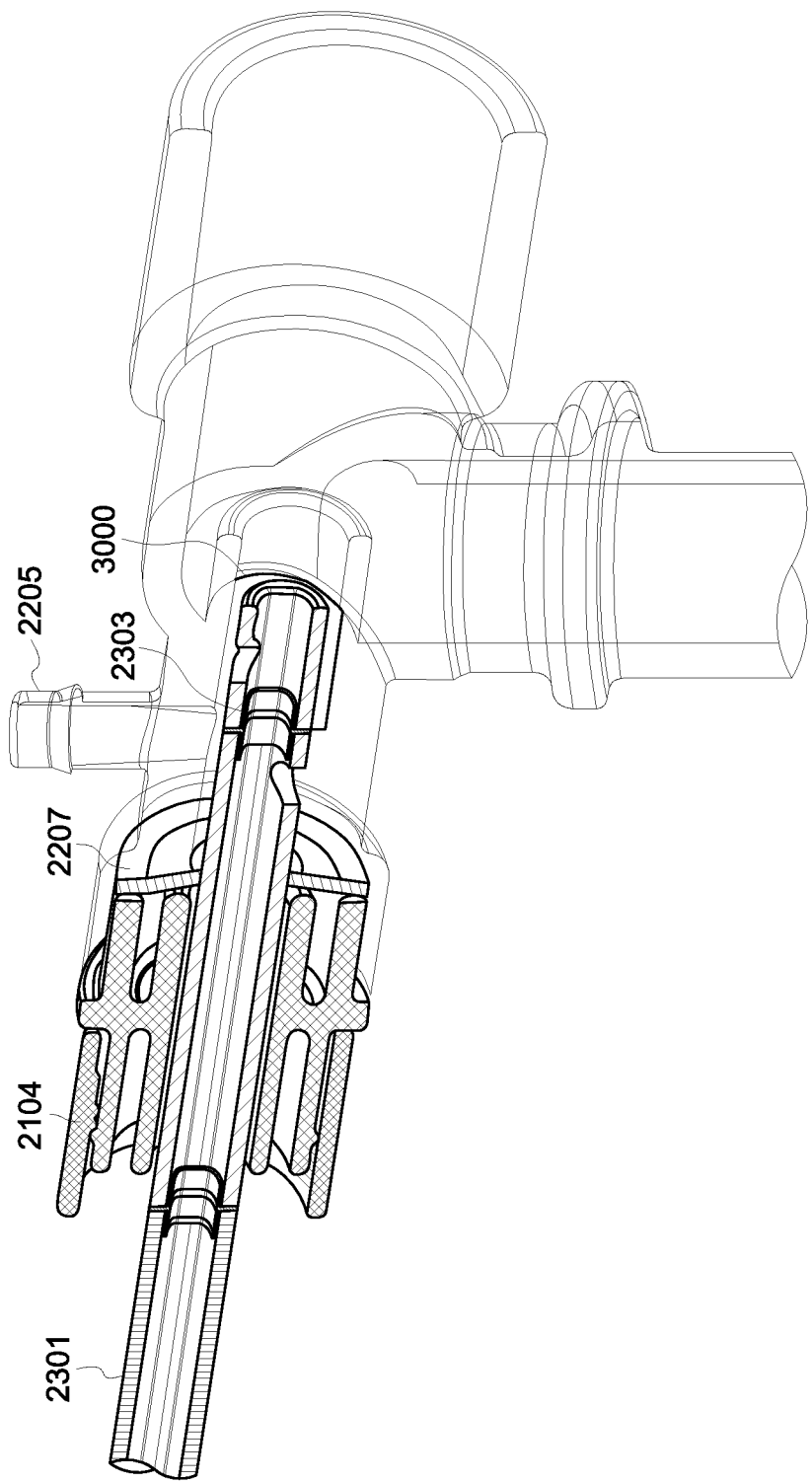
FIG. 23 is an isometric internal view of the endotracheal tube connector end.

In FIGS. 22A and 23, the endotracheal tube connector 2107 is shown in detail. Connector 2107 includes ports 2201 which connects to an ETT, and 2203 configured to secure to a ventilator. Further, the connector 2107 includes a catheter cleaning port 2205. Disposed on the interior of the connector 2107 is a gasket 2207 that is configured to prevent ventilated air from going into a sterile bag. The gasket 2207 is configured to whip mucous off of the outside surface of the catheter. This feature is believed novel of the present invention and is a benefit over the prior art.

Figure 22B:
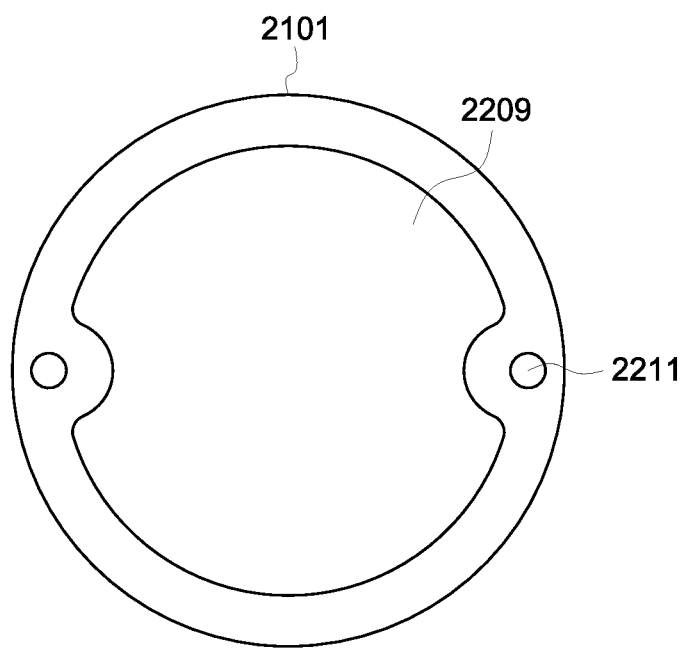
FIG. 22B is a cross sectional view of the catheter of FIG. 22.

In FIG. 22B, a cross sectional view is taken from line A of catheter 2101. As shown, the lumen 2209 formed by catheter 2101 has one or more cabling holes 2211 wherein the cable/wire is extended through.

As better shown in FIG. 23, the attachment mechanism 2104 is configured to provide an area wherein a sterile bag cover (not shown) can be secured over the catheter 2101 and between the catheter and attachment mechanism 2104. In addition, couplers 2303 are positioned within catheter 2101 which provide for places for the cables to attach to within the catheter. Also these couplers enable the connection of catheter 2301 to connect to a softer durometer catheter tip 3000.

Figure 24:
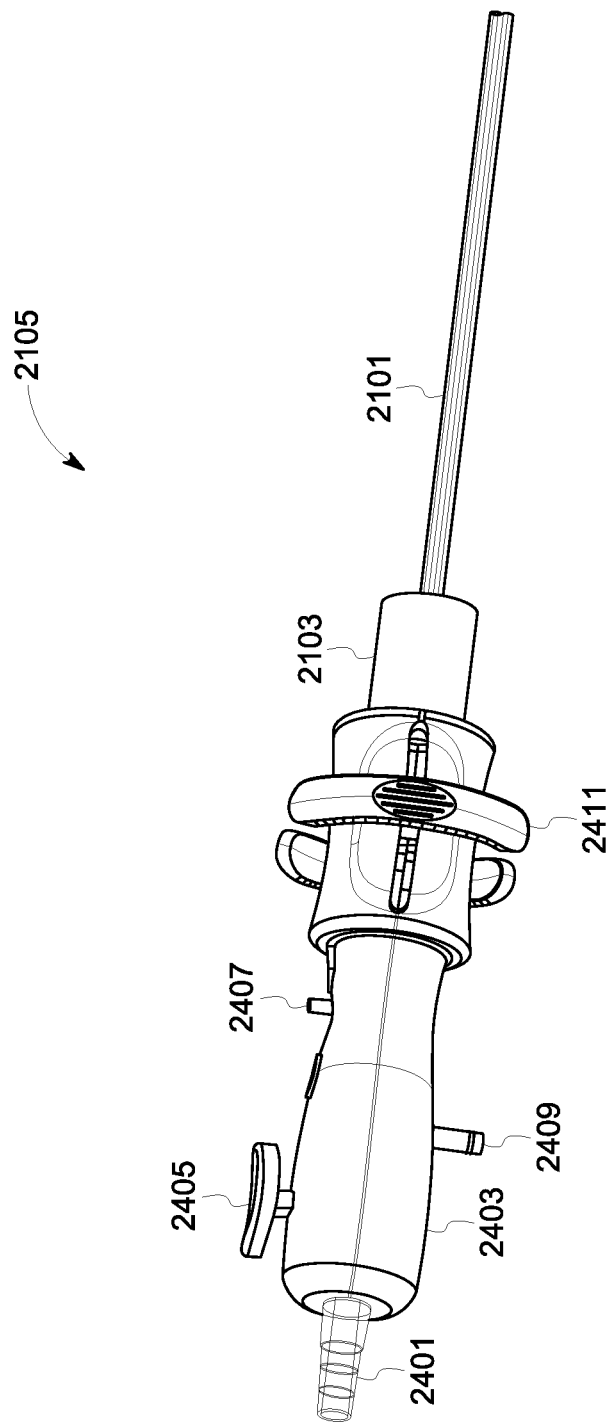
FIG. 24 is an isometric view of a controller end of the endobronchial suctioning device of FIG. 21.

In FIG. 24, control end 2105 is shown. Control end 2105 includes a suction nozzle 2401 extending away from a body 2403 of the control end. A suction button 2405 extends from body 2403 and is configured to activate and deactivate suction based on the desired needs of the user, the suction being facilitated through a suction chamber. The control end 2105 further includes a suction locking switch 2407 configured to lock suction control. A BAL port 2409 is further provided. As will be discussed in more detail, the control end 2105 further includes a control lever 2411 which is connected to the cables and configured to provide for rotational control of the cables. The control lever 2411 provides for improved user control of the apparatus.

Figure 25:
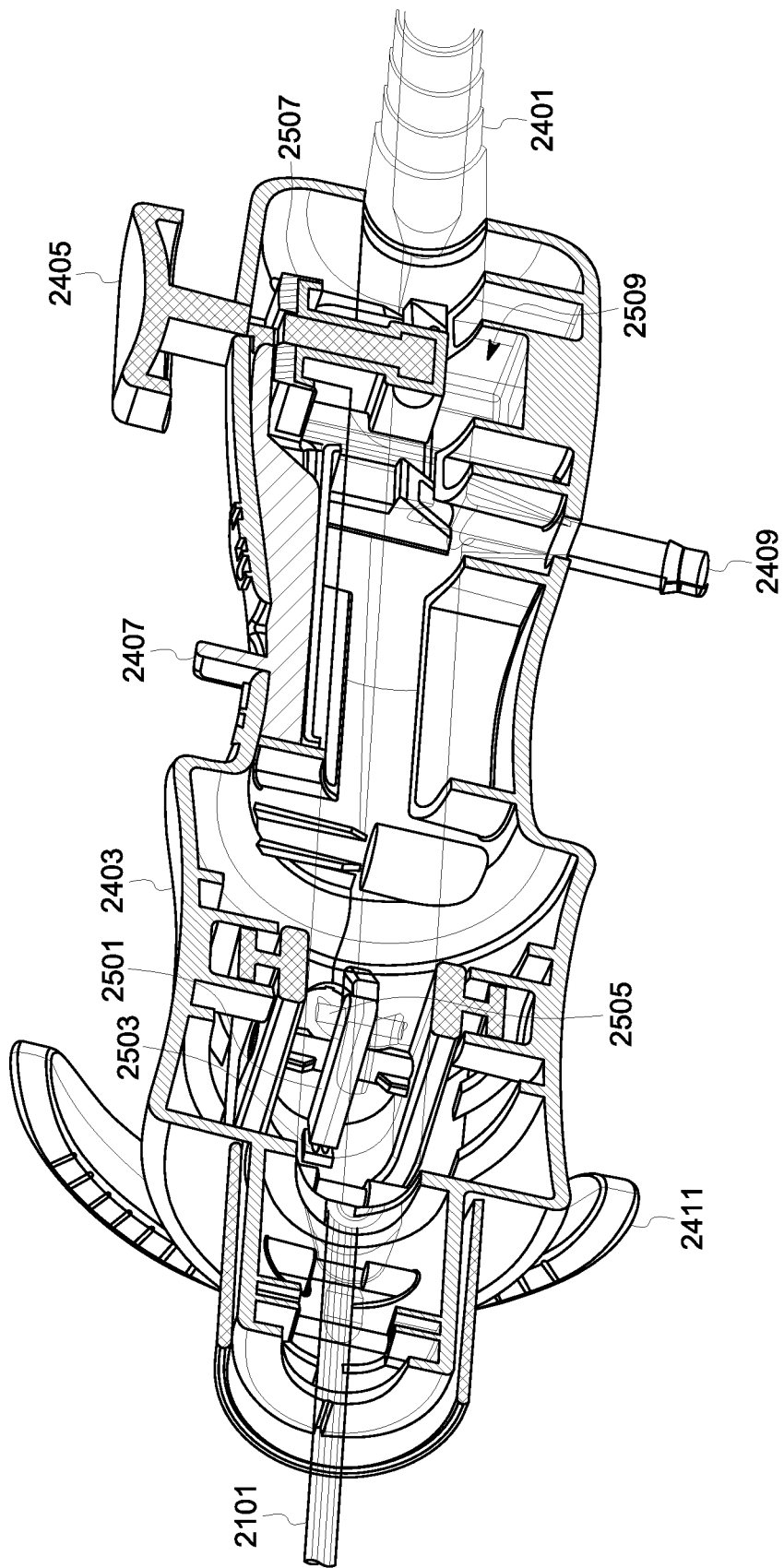
FIG. 25 is an isometric internal view of the controller end.

In FIG. 25, an internal view of control end 2105 is shown. In this embodiment, the suction button 2405 is engaged with a suction plunger 2507 to control suction via the suction nozzle 2401. It should be appreciated that the suction button and plunger can be manipulated to open the flow of suction.

As shown, the locking switch 2407 is configured to engage with the suction button 2405 to lock the suction button in an outward configuration to prevent suction activation. The control end 2105 further includes an attachment point 2503 for the wire to secure to. In the preferred embodiment, an articulating lever 2501 is in physical communication with the control lever 2411 and in connection with an actuation lever stay pin 2505. The cables are controlled via manipulation of the articulating lever. The control lever 2411 is configured to function similar to the circular disk described above to manipulate movement of the cables through the catheter.

FIG. 26 depicts an exploded view of an alternative embodiment of the control end 2105 for clarity. As shown, the articulating control 2411 includes a rotational pin 2605 which allows for the control 2411 to be rotationally manipulated via the user. The control end 2105 further having articulating internal arms forming lever 2501 and an articulating arms stay pin housing 2601 forming the grove and hole wherein stay pin 2505 enters. Further included is a control mechanism suction manifold 2603 that consists of the suction end, suction button housing, BAL port, and connects to suction catheter 2101.

Figure 27:
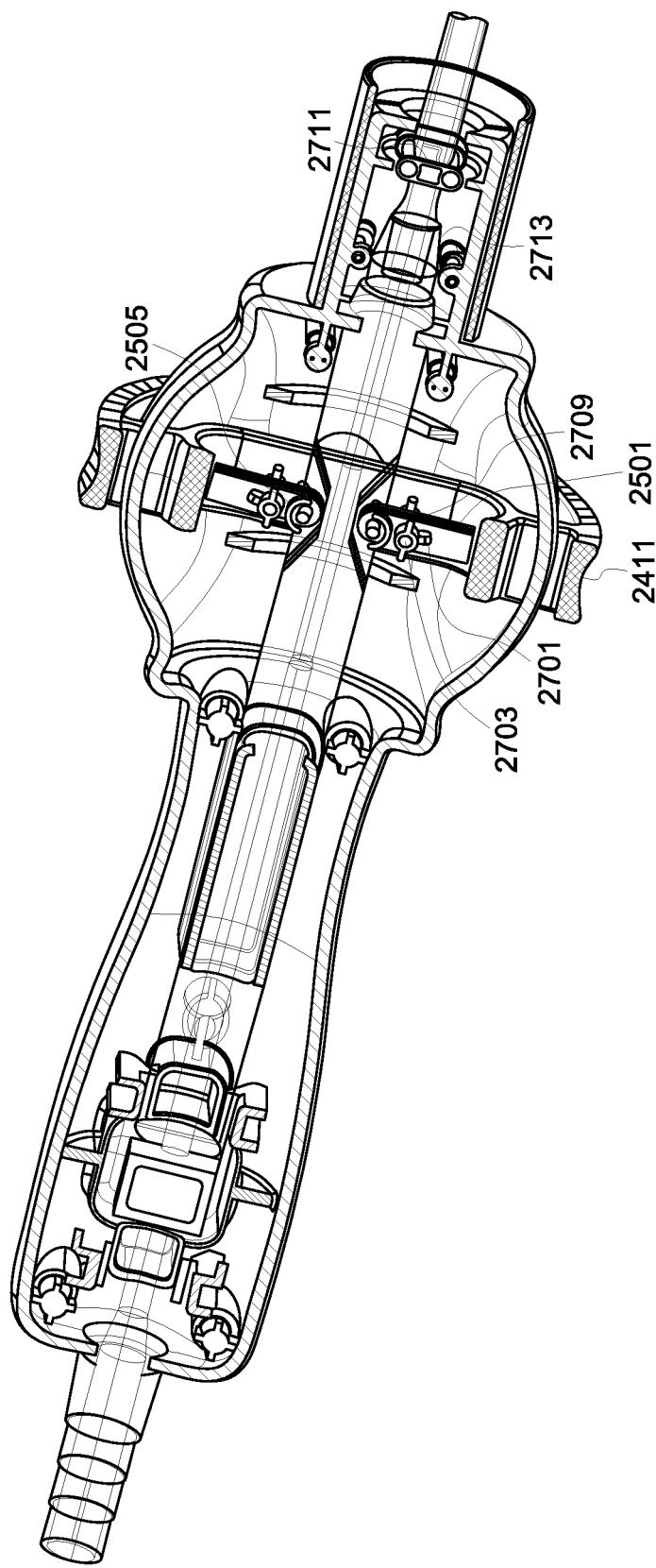
FIG. 27 is an isometric internal view of the controller end of FIG. 26.

FIG. 27 further depicts an internal view of the control end 2105, having sliding groves 2701 with sliding grove pins 2703 extending therethrough. Articulating lever 2501, which have grooves 2709 for engagement of the wire at attachment point 2503, and articulating lever arm stay pins 2505 are attached to the articulating control, which provides for user manipulation of the cables.

The system includes articulating wire guide pins 2711 for receiving and guiding the wire within the system. In this embodiment, an attachment point 2713 is provided for attachment of the catheter and internal suction manifold.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A bi-lateral endobronchial suctioning device, comprising:
   an interface capable of manipulation by a provider to control bronchial suctioning of an intubated patient, the interface including a control ring coupled to a fulcrum pin and a plurality of cables;
   a catheter portion that includes layered tubes within which the plurality of cables are disposed, and an articulation joint portion formed in a portion of a middle tube in the layered tubes by a plurality of grooves in a surface of the middle tube, the articulation joint portion actuated by the interface so that angular movement of the control ring flexes the plurality of cables in opposing directions to in turn flex the articulation joint portion about the plurality of grooves;
   a distal articulating tip that is manipulated in a desired direction when the control ring is actuated to flex the articulation joint portion; and
   a port coupled to a side of the catheter portion for bronchoalveolar lavage of the intubated patient,
   wherein the provider actuates the control ring to maneuver the distal articulating tip to perform the bronchial suctioning from both the left bronchus and the right bronchus.

2. The bi-lateral endobronchial suctioning device of claim 1, wherein the interface further comprises a button to initiate and terminate suctioning of bronchial secretions from the intubated patient.

3. The bi-lateral endobronchial suctioning device of claim 1, further comprising a suction nozzle positioned near the interface and through which secretions exit the bi-lateral endobronchial suction device after bronchial suctioning.

4. The bi-lateral endobronchial suctioning device of claim 1, further comprising a means for coupling the bi-lateral endobronchial suction device to one or more of a ventilator machine, an end of an endotracheal tube, and/or to a catheter cleaning system.

5. The bi-lateral endobronchial suctioning device of claim 4, wherein the means for coupling is a manifold forming a chamber coupled to a port.

6. The bi-lateral endobronchial suctioning device of claim 1, wherein the interface is configured to operate the device in an endotracheal tube for use on the intubated patient.

7. The bi-lateral endobronchial suctioning device of claim 1, wherein the distal articulating tip includes one or more components that enable the distal articulating tip to be detected by an external probe.

8. The bi-lateral endobronchial suctioning device of claim 1, wherein the distal articulating tip includes one or more orifices that enable secretions suctioned by the bi-lateral endobronchial suction device to pass through the catheter portion.

9. The bi-lateral endobronchial suctioning device of claim 1, wherein the port coupled to a side of the catheter portion for bronchoalveolar lavage includes a tubular extension through which a fluid is applied to the catheter portion to flow into the lung, and a cap to prevent air from entering the catheter system when removing secretions through suctioning.

10. The bi-lateral endobronchial suctioning device of claim 1, wherein the articulation joint portion includes a plurality of fitted pieces partially separated by the plurality of grooves in the surface of the middle tube, wherein the plurality of cables run along the catheter portion to a fitted piece furthest from the interface.

* * * * *